(12) United States Patent
Isogai et al.

(10) Patent No.: US 7,560,541 B2
(45) Date of Patent: Jul. 14, 2009

(54) HEART20049410 FULL-LENGTH CDNA AND POLYPEPTIDES

(75) Inventors: Takao Isogai, Ibaraki (JP); Tomoyasu Sugiyama, Tokyo (JP); Tetsuji Otsuki, Chiba (JP); Ai Wakamatsu, Chiba (JP); Hiroyuki Sato, Osaka (JP); Shizuko Ishii, Chiba (JP); Jun-ichi Yamamoto, Chiba (JP); Yuuko Isono, Chiba (JP); Yuri Hio, Chiba (JP); Kaoru Otsuka, Saitama (JP); Keiichi Nagai, Tokyo (JP); Ryotaro Irie, Chiba (JP); Ichiro Tamechika, Osaka (JP); Naohiko Seki, Chiba (JP); Tsutomu Yoshikawa, Chiba (JP); Motoyuki Otsuka, Tokyo (JP); Kenji Nagahari, Tokyo (JP); Yasuhiko Masuho, Tokyo (JP)

(73) Assignee: Acceleron Pharma, Inc., Cambridge, MA (US)

( * ) Notice: Subject to any disclaimer, the term of this patent is extended or adjusted under 35 U.S.C. 154(b) by 0 days.

(21) Appl. No.: 11/767,852

(22) Filed: Jun. 25, 2007

(65) Prior Publication Data

US 2008/0032304 A1 Feb. 7, 2008

Related U.S. Application Data

(62) Division of application No. 11/293,697, filed on Dec. 5, 2005, which is a division of application No. 10/108,260, filed on Mar. 28, 2002, now Pat. No. 7,193,069.

(30) Foreign Application Priority Data

Mar. 22, 2002 (JP) ............................. 2002-137785

(51) Int. Cl.
*C07H 21/04* (2006.01)
*C12N 15/00* (2006.01)
*C12N 1/00* (2006.01)

(52) U.S. Cl. .................... 536/23.5; 435/320.1; 435/243

(58) Field of Classification Search ....................... None
See application file for complete search history.

(56) References Cited

U.S. PATENT DOCUMENTS

| | | | | |
|---|---|---|---|---|
| 4,647,529 A | * | 3/1987 | Rodland et al. ................ 435/6 |
| 5,474,796 A | * | 12/1995 | Brennan ................... 427/2.13 |
| 5,935,852 A | | 8/1999 | Follettie et al. |
| 6,133,232 A | | 10/2000 | De Robertis et al. |
| 6,265,165 B1 | | 7/2001 | Xu et al. |
| 6,610,510 B1 | | 8/2003 | Valenzuela et al. |
| 2002/0164682 A1 | | 11/2002 | Follettie et al. |
| 2003/0134790 A1 | | 7/2003 | Langenfeld |
| 2003/0194704 A1 | | 10/2003 | Penn et al. |
| 2003/0199042 A1 | | 10/2003 | Valenzuela et al. |
| 2004/0005560 A1 | | 1/2004 | Isogai et al. |
| 2004/0181033 A1 | | 9/2004 | Han et al. |
| 2005/0186663 A1 | * | 8/2005 | Davies et al. ............. 435/69.5 |

| | | |
|---|---|---|
| 2006/0105376 A1 | 5/2006 | Isogai et al. |

FOREIGN PATENT DOCUMENTS

| | | |
|---|---|---|
| EP | 1026242 A1 | 9/2000 |
| EP | 1347046 | 9/2003 |
| WO | WO-97/48275 | 12/1997 |
| WO | WO-98/34951 | 8/1998 |
| WO | WO-98/49296 | 11/1998 |
| WO | WO-99/01553 | 1/1999 |
| WO | WO-99/40181 | 8/1999 |
| WO | WO-00/55193 | 9/2000 |
| WO | WO 01/53312 A1 | 7/2001 |
| WO | WO 01/57182 A3 | 8/2001 |
| WO | WO 01/57185 A2 | 8/2001 |
| WO | WO-02/10214 | 2/2002 |
| WO | WO-02/32929 | 4/2002 |
| WO | WO-02/054940 | 7/2002 |
| WO | WO-02/077204 | 10/2002 |
| WO | WO-02/078516 | 10/2002 |
| WO | WO-02/090992 | 11/2002 |
| WO | WO-03/055443 | 1/2003 |
| WO | WO-03/012082 | 2/2003 |
| WO | WO-03/055911 | 7/2003 |
| WO | WO-03/072714 | 9/2003 |
| WO | WO-03/106657 | 12/2003 |
| WO | WO-2004/074460 | 9/2004 |
| WO | WO-2005/003158 | 1/2005 |

OTHER PUBLICATIONS

Bodian, D.L., "IBLAST, a fully automated method for cDNA cloning in silico," 1999, Faseb J, p. A1382, vol. 13, No. 7.
EMBL Accession No. AF039235; XP-002206836; Jan. 17, 1998.
GenBank Accession No. AC079860 (GI:11990750), "Homo sapiens chromosome RPCI-11 clone RP11-671C15, Working Draft," Dec. 23, 2000, [online, retrieved Jun. 3, 2004] <URL:http://www.ncbi.nlm.nih.gov/entrez/viewer.fcgi?db=nucleotide&val=11990750>.
GENSEQ Accession No. AAM82707; XP-002206837; Nov. 7, 2001.
GENSEQ Accession No. AA158813, XP-002206834; Oct. 22, 2001.
GENSEQ Accession No. AAM39657; XP-002206835; Oct. 22, 2001.

(Continued)

*Primary Examiner*—Bradley L Sisson
(74) *Attorney, Agent, or Firm*—Ropes & Gray LLP

(57) ABSTRACT

Novel full-length cDNAs are provided. cDNA derived from human have been isolated. The full-length nucleotide sequences of the cDNA and amino acid sequences encoded by the nucleotide sequences have been determined. Because the cDNA of the present invention are full-length and contain the translation start site, they provide information useful for analyzing the functions of the polypeptide.

8 Claims, 1 Drawing Sheet

OTHER PUBLICATIONS

Gill et al., "A new dynamic tool to perform assembly of Expressed Sequence Tags (ESTs)," 1997, Comput Appl Biosci; pp. 453-457, vol. 14, No. 4.

Homology Search Result Date (homology search result of the clones disclosed in present application) pp. 1-74, Dec. 14, 2001.

O'Brien et al., "Characterization of Five Novel Human Genes in the 11q13-q22 Region," 2000, Biochem Biophys Res Commun, pp. 90-94, vol. 273, No. 1.

Ota et al., "Complete Sequencing and Characterization of 21,243 Full-Length Human cDNAs," Nature Genetics, vol. 36, No. 1, Jan. 2004, pp. 40-45.

Sugano et al., Tanpakushitsu Kakusan Koso (Protein, Nucleic Acid and Enzyme), vol. 38, No. 3, pp. 4761-4781 (1993) English language abstract provided.

Suzuki et al., "Construction and characterization of a full length-enriched and a 5'-end enriched cDNA library," 1997, Gene, pp. 149-156, vol. 200, No. 1-2.

SWISSPROT Accession No. Q9BTE6; XP-002206838; Jun. 1, 2001.

Avsian-Kretchmer et al., "Comparative geneomic analysisof the eight-membered ring cystine knot-containing bone morphogenetic protein antagonists," Molecular Endocrinology 18(1):1-12 (2004).

Belo et al., "*Cerberus-like* is a secreted factor with nerualizing activity expressed in the anterior primitive endoderm of the mouse gastrula," Mechanisims of Development 68:45-57 (1997).

Biben et al., "Murine Cerberus Homologue mCer-1: A canadidate anterior patterning molecule," Development Biology 194:135-151 (1998).

Bouwmeester et al., "Cerberus is a head-inducing secreted factor expressed in the anterior endoderm of Spemann's organizer," Nature 382:595-601 (1996).

Esteban et al., "The novel Cer-like protein Caronte mediates the extablishment of embryonic left-right asymmetry," Nature 401:243-251 (1999).

Katoh et al., "Identification and characterization of human *CKTSF1B2* and *CKTSF1B3* genes in silico," Oncology Reports 12:423-427 (2004).

Kuroda et al., "Neural Induction in *Xenopus*: requirement for extodermal and endomesodermal signals via chordin, noggin, β-catenin and cerberus," PLoS Biology 2(5):0623-0634 (2004).

Lah et al., "Human *cerberus* related gene *CER1* maps to chromosome 9," Genomics 55:364-366 (1999).

Marques et al., "The activity of the nodal antagonist *Cerl-2* in the mouse node is required for correct L/R body axis," Genes & Development 18:2342-2347 (2004).

Pearce et al., "A mouse cerberus/dan-related gene family," Developmental Biology 209:98-110 (1999).

Piccolo et al., "The head inducer Cerberus is a multifunctional antagonist of Nodal, BMP and Wnt signals," Nature 397:707-710 (1999).

Silva et al., "Endogenous Cerberus activity is required for anterior head specification in *Xenopus*," Development 130(20):4943-4953 (2003).

Stanley et al., "Murine *cerberus* homologue *Cer1* maps to chromosome 4," Genomics 49:337-338 (1998).

* cited by examiner

HEART20049410 FULL-LENGTH CDNA AND POLYPEPTIDES

CROSS REFERENCE TO RELATED APPLICATIONS

This application is a Division of U.S. application Ser. No. 11/293,697, filed Dec. 5, 2005, which is a Division of U.S. application Ser. No. 10/108,260, filed Mar. 28, 2002, which claims priority from Japanese patent application JP 2002-137785, filed Mar. 22, 2002. The entire contents of the aforementioned applications are incorporated herein in their entirety by reference.

FIELD OF THE INVENTION

The present invention relates to polynucleotides encoding novel polypeptides, polypeptides encoded by the polynucleotides, and new uses of these.

BACKGROUND OF THE INVENTION

Currently, the sequencing projects, the determination and analysis of the genomic DNA of various living organisms have been in progress all over the world. The whole genomic sequences of more than 40 species of prokaryotes, a lower eukaryote, yeast, a multicellular eukaryote, *C. elegans*, and a higher plants, *arabidopsis*, etc. are already determined. For human genome, presumably having 3 billion base pairs, the analysis was advanced under global cooperative organization, and a draft sequence was disclosed in 2001. Moreover, all the structures are to be clear and to be disclosed in 2002-2003. The aim of the determination of genomic sequence is to reveal the functions of all genes and their regulation and to understand living organisms as a network of interactions between genes, proteins, cells or individuals through deducing the information in a genome, which is a blueprint of the highly complicated living organisms. To understand living organisms by utilizing the genomic information from various species is not only important as an academic subject, but also socially significant from the viewpoint of industrial application.

However, determination of genomic sequences itself cannot identify the functions of all genes. For example, as for yeast, only the function of approximately half of the 6000 genes, which is predicted based on the genomic sequence, was able to be deduced. On the other hand, the human genome has been estimated to contain about 30,000-40,000 genes. Further, 100,000 or more types of mRNAs are said to exist when variants produced by alternative splicing are taken into consideration. Therefore, it is desirable to establish "a high throughput analysis system of the gene functions" which allows us to identify rapidly and efficiently the functions of vast amounts of the genes obtained by the genomic sequencing.

Many genes in the eukaryotic genome are split by introns into multiple exons. Thus, it is difficult to predict correctly the structure of encoded protein solely based on genomic information. In contrast, cDNA, which is produced from mRNA that lacks introns, encodes a protein as a single continuous amino acid sequence and allows us to identify the primary structure of the protein easily. In human cDNA research, to date, more than three million ESTs (Expression Sequence Tags) are publicly available, and the ESTs presumably cover not less than 80% of all human genes.

The information of ESTs is utilized for analyzing the structure of human genome, or for predicting the exon-regions of genomic sequences or their expression profile. However, many human ESTs have been derived from proximal regions to the 3'-end of cDNA, and information around the 5'-end of mRNA is extremely little. Among human cDNAs, the number of the corresponding mRNAs whose encoding full-length protein sequences are deduced is approximately 13,000.

It is possible to identify the transcription start site of mRNA on the genomic sequence based on the 5'-end sequence of a full-length cDNA, and to analyze factors involved in the stability of mRNA that is contained in the cDNA, or in its regulation of expression at the translation stage. Also, since a full-length cDNA contains atg codon, the translation start site, in the 5'-region, it can be translated into a protein in a correct frame. Therefore, it is possible to produce a large amount of the protein encoded by the cDNA or to analyze biological activity of the expressed protein by utilizing an appropriate expression system. Thus, analysis of a full-length cDNA provides valuable information which complements the information from genome sequencing. Also, full-length cDNA clones that can be expressed are extremely valuable in empirical analysis of gene function and in industrial application.

Therefore, if a novel human full-length cDNA is isolated, it can be used for developing medicines for diseases in which the gene is involved. The protein encoded by the gene can be used as a drug by itself. Thus, it has great significance to obtain a full-length cDNA encoding a novel human protein.

In particular, human secretory proteins or membrane proteins would be useful by itself as a medicine like tissue plasminogen activator (TPA), or as a target of medicines like membrane receptors. In addition, genes for signal transduction-related proteins (protein kinases, etc.), glycoprotein-related proteins, transcription-related proteins, etc. are genes whose relationships to human diseases have been elucidated. Moreover, genes for disease-related proteins form a gene group rich in genes whose relationships to human diseases have been elucidated.

Therefore, it has great significance to isolate novel full-length cDNA clones of human, only few of which has been isolated. Especially, isolation of a novel cDNA clone encoding a secretory protein or membrane protein is desired since the protein itself would be useful as a medicine, and also the clones potentially include a gene involved in diseases. In addition, genes encoding proteins that are involved in signal transduction, glycoprotein, transcription, or diseases are expected to be useful as target molecules for therapy, or as medicines themselves. These genes form a gene group predicted to be strongly involved in diseases. Thus, identification of the full-length cDNA clones encoding those proteins has great significance.

SUMMARY OF THE INVENTION

An objective of the present invention is to provide polynucleotides encoding novel polypeptides, polypeptides encoded by the polynucleotides, and novel usages of these.

In particular, the disclosure provides the nucleic acid sequence of clone HEART20049410, the coding sequence thereof (SEQ ID NO:1; SEQ ID NO:971 from prior application) and the encoded polypeptide (SEQ ID NO:2; SEQ ID NO:3414 from prior application).

The inventors have developed a method for efficiently cloning, from a cDNA library having very high fullness-ratio, a human full-length cDNA that is predicted to be a full-length cDNA clone, where the cDNA library is synthesized by an improved method (WO 01/04286) of the oligo-capping method (K. Maruyama and S. Sugano, Gene, 138: 171-174

(1994); Y. Suzuki et al., Gene, 200: 149-156 (1997)). Then, the nucleotide sequences of cDNA clones whose fullness ratio is high, obtained by this method, were determined mainly from their 5'-ends, and, if required, from 3'-ends.

Further, representative clones, which were estimated to be novel and full-length, among the clones obtained, were analyzed for their full-length nucleotide sequences. The determined full-length nucleotide sequences were analyzed by BLAST homology search of the databases shown below. Because the homology search of the present invention is carried out based on the information of full-length cDNAs including the entire coding regions, homology to every part of a polypeptide can be analyzed. Thus, in the present invention, the reliability of homology search has been greatly improved.

[1] SwissProt (avalible on the world wide web at ebi.ac.uk/ebi_docsSwissProt_db/swisshome.html),
[1] GenBank (avalible on the world wide web at ncbi.nlm.nih.gov/web/GenBank),
[3] UniGene (Human) (avalible on the world wide web at ncbi.nlm.nih.gov/UniGene), and
[4] nr (a protein database, which has been constructed by combining data of coding sequences (CDS) in nucleotide sequences deposited in GenBank, and data of SwissProt, PDB (avalible on the world wide web at rcsb.org/pdb/index.html), PIR (http://pir.georgetown.edu/pirwww/pirhome.shtml), and PRF (avalible on the world wide web at prf.or.jp/en/); overlapping sequences have been removed.)

Further, the gene expression profiles of cDNA clones whose full-length nucleotide sequence had been determined were studied by analyzing the large-scale cDNA database constructed based on the 5'-end nucleotide sequences of cDNAs obtained. In addition to the analysis for the expression profile by computer, the profiles of gene expression in living cells were also determined by PCR. The present inventors revealed the usefulness of the genes of the present invention based on these analysis results.

In the present invention, gene functions were revealed by the analysis of expression profiles in silico based on the information of full-length nucleotide sequences. The expression profiles used in the expression frequency analysis were studied based on the database containing sufficient amount of fragment sequence data. The expression frequency analysis was carried out by referring, for these expression profiles, to the full-length nucleotide sequences of many cDNA clones obtained in the present invention. Thus, a highly reliable analysis can be achieved by referring to the full-length nucleotide sequences of a wide variety of genes for the sufficiently large population for analysis (expression profiles). Namely, the results of expression frequency analysis using the full-length sequences of the present invention more precisely reflect the gene expression frequency in tissues and cells from which a certain cDNA library was derived. In other words, the information of full-length cDNA nucleotide sequence of the present invention made it possible to achieve the highly reliable expression frequency analysis.

The full-length cDNA clones of this invention were obtained by the method comprising the steps of [1] preparing libraries containing cDNAs with the high fullness ratio by oligo-capping, and [2] assembling 5'-end sequences and selecting one with the highest probability of completeness in length in the cluster formed (there are many clones longer in the 5'-end direction). However, the uses of primers designed based on the 5'- and 3'-end sequences of polynucleotides provided by the present invention enable readily obtaining full-length cDNAs without such a special technique. The primer, which is designed to be used for obtaining cDNAs capable of being expressed, is not limited to the 5'- and 3'-end sequences of polynucleotide.

Specifically, the present invention relates to a polynucleotide selected from the group consisting of the following (a) to (g):

(a) a polynucleotide comprising a protein-coding region of the nucleotide sequence of any one of SEQ ID NOs shown in Table 1;

(b) a polynucleotide encoding a polypeptide comprising the amino acid sequence of any one of SEQ ID NOs shown in Table 1;

(c) a polynucleotide comprising a nucleotide sequence encoding a polypeptide comprising the amino acid sequence of any one of SEQ ID NOs shown in Table 1, wherein, in said amino acid sequence, one or more amino acids have been substituted, deleted, inserted, and/or added, and wherein said nucleotide sequence encodes a polypeptide functionally equivalent to a polypeptide comprising the selected amino acid sequence;

(d) a polynucleotide hybridizing under stringent conditions to a polynucleotide comprising the nucleotide sequence of any one of SEQ ID NOs shown in Table 1, wherein said nucleotide sequence encodes a polypeptide functionally equivalent to a polypeptide encoded by the selected nucleotide sequence;

(e) a polynucleotide comprising a nucleotide sequence encoding a partial amino acid sequence of a polypeptide encoded by the polynucleotide according to any one of (a) to (d); (f) a polynucleotide comprising a nucleotide sequence having at least 70% identity to the nucleotide sequence of (a); and (g) a polynucleotide comprising a nucleotide sequence having at least 90% identity to the nucleotide sequence of (a).

The present invention also relates to a polypeptide encoded by the above-mentioned polynucleotide or a partial peptide thereof, an antibody binding to the polypeptide or the peptide, and a method for immunologically assaying the polypeptide or the peptide, which comprises the steps of contacting the polypeptide or the peptide with the antibody, and observing the binding between the two.

Furthermore, the present invention features a vector comprising the above-mentioned polynucleotide, a transformant carrying the polynucleotide or the vector, a transformant carrying the polynucleotide or the vector in an expressible manner, and a method for producing the polypeptide or the peptide, which comprises the steps of culturing the transformant and recovering an expression product.

Another feature of the present invention is an oligonucleotide comprising at least 15 nucleotides, said oligonucleotide comprising a nucleotide sequence complementary to the nucleotide sequence of SEQ ID NO: 1 or to a complementary strand thereof. This oligonucleotide can be used as a primer for synthesizing the above-mentioned polynucleotide or used as a probe for detecting the polynucleotide. The present invention includes an antisense polynucleotide against the polynucleotide or a part thereof, and a method for detecting the polynucleotide, which comprises the following steps of:
a) incubating a target polynucleotide with the oligonucleotide under hybridizable conditions, and
b) detecting hybridization of the target polynucleotide with the oligonucleotide.

Still another feature of the present invention is a database of polynucleotides and/or polypeptides, said database comprising information on the nucleotide sequence of SEQ ID NO: 1 and/or on the amino acid sequences of SEQ ID NO: 2.

Herein, "polynucleotide" is defined as a molecule, such as DNA and RNA, in which multiple nucleotides are polymerized. There are no limitations on the number of the polymerized nucleotides. In case that the polymer contains relatively low number of nucleotides, it is also described as an "oligonucleotide", which is included in the "polynucleotide" of the present invention. The polynucleotide or the oligonucleotide of the present invention can be a natural or chemically synthesized product. Alternatively, it can be synthesized using a template polynucleotide by an enzymatic reaction such as PCR. Furthermore, the polynucleotide of the present invention may be modified chemically. Moreover, not only a single-strand polynucleotide but also a double-strand polynucleotide is included in the present invention. In this specification, especially in claims, when the polynucleotide is described merely as "polynucleotide", it means not only a single-strand polynucleotide but also a double-strand polynucleotide. When it means double-strand polynucleotide, the nucleotide sequence of only one chain is indicated. However, based on the nucleotide sequence of a sense chain, the nucleotide sequence of the complementary strand thereof is essentially determined.

As used herein, an "isolated polynucleotide" is a polynucleotide the structure of which is not identical to that of any naturally occurring polynucleotide or to that of any fragment of a naturally occurring genomic polynucleotide spanning more than three separate genes. The term therefore includes, for example, (a) a DNA which has the sequence of part of a naturally occurring genomic DNA molecule in the genome of the organism in which it naturally occurs; (b) a polynucleotide incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion polypeptide. Specifically excluded from this definition are polynucleotides of DNA molecules present in mixtures of different (i) DNA molecules, (ii) transfected cells, or (iii) cell clones; e.g., as these occur in a DNA library such as a cDNA or genomic DNA library.

The term "substantially pure" as used herein in reference to a given protein or polypeptide means that the protein or polypeptide is substantially free from other biological macromolecules. For example, the substantially pure protein or polypeptide is at least 75%, 80%, 85%, 95%, or 99% pure by dry weight. Purity can be measured by any appropriate standard method known in the art, for example, by column chromatography, polyacrylamide gel electrophoresis, or HPLC analysis.

All the cDNAs provided by the present invention are full-length cDNAs. The "full-length cDNA" herein means that the cDNA contains the ATG codon, which is the start point of translation therein. The untranslated regions upstream and downstream of the protein-coding region, both of which are naturally contained in natural mRNAs, are not indispensable. It is preferable that the full-length cDNAs of the present invention contain the stop codon.

DETAILED DESCRIPTION OF THE INVENTION

Figure 1:
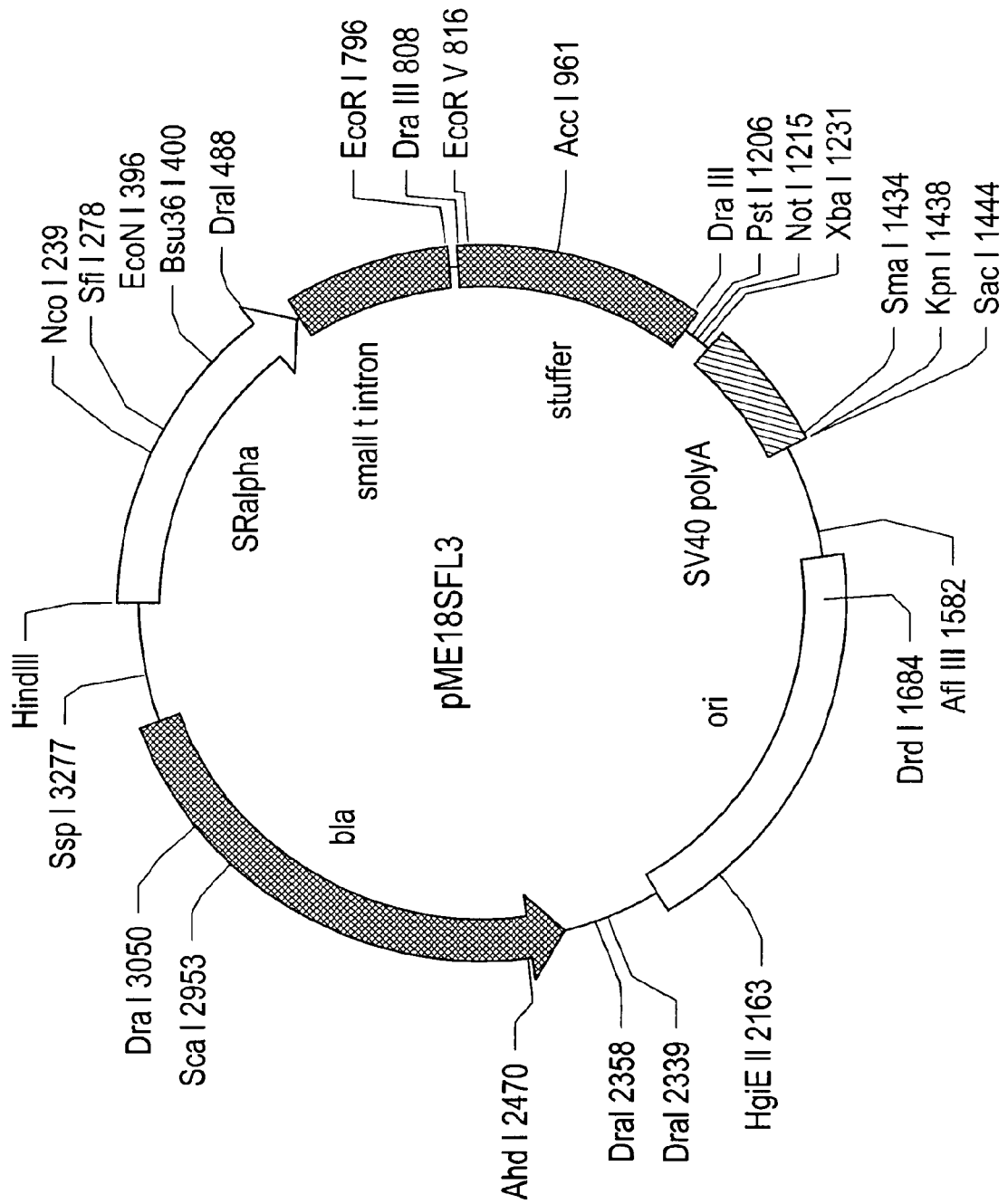
FIG. 1 shows the restriction map of the vector pME18SFL3.

All the clones (2443 clones) of the present invention are novel and encode the full-length polypeptides. Further, all the clones are cDNAs with the high fullness ratio, which were obtained by oligo-capping method, and also clones which are not identical to any of known human mRNAs (namely, novel clones) selected by searching, for the 5'-end sequences, mRNA sequences with the annotation of "complete cds" in the GenBank and UniGene databases by using the BLAST homology search [S. F. Altschul, W. Gish, W. Miller, E. W. Myers & D. J. Lipman, J. Mol. Biol., 215: 403-410 (1990); W. Gish & D. J. States, Nature Genet., 3: 266-272 (1993)]; they are also clones that were assumed to have higher fullness ratio among the members in the cluster formed by assembling. Most of the clones assessed to have high fullness ratio in the cluster had the nucleotide sequences longer in the 5'-end direction.

All the full-length cDNAs of the present invention can be synthesized by a method such as PCR (Current protocols in Molecular Biology edit. Ausubel et al. (1987) Publish. John Wiley & Sons Section 6.1-6.4) using primer sets designed based on the 5'-end and 3'-end sequences or using primer sets of primers designed based on the 5'-end sequences and a primer of oligo dT sequence corresponding to poly A sequence. Table 1 contains the clone name of full-length cDNA of a selected clone of the present invention, the SEQ ID NO of the full-length nucleotide sequence, the CDS portion deduced from the full-length nucleotide sequence, and the SEQ ID NO of the translated amino acid. The position of the CDS is shown according to the rule of "DDBJ/EMBL/GenBank Feature Table Definition" (avalible on the world wide web at ncbi.nlm.nih.gov/collab/FT/index.html). The start position number corresponds to the first letter of "ATG" that is the nucleotide triplet encoding methionine; the termination position number corresponds to the third letter of the stop codon. These are indicated being flanked with the mark "..". However, with respect to the clones having no stop codon, the termination position is indicated by the mark ">" according to the above rule.

TABLE 1

| Clone name | SEQ ID NO. of nucleotide sequence | Position of CDS | SEQ ID NO. of amino acid sequence |
| --- | --- | --- | --- |
| HEART20049410 | 1 | 44 ... 613 | 2 |

Namely, primers used to synthesize polynucleotides can be designed based on the nucleotide sequences of polynucleotides of the present invention shown in SEQ ID NO: 1. When one intends to synthesize full-length cDNAs, an oligo dT primer can be used as the 3'-end primer. The length of the primers is usually 15-100 bp, and favorably between 15-35 bp. In case of LA PCR, which is described below, the primer length of 25-35 bp may provide a good result.

A method to design a primer that enables a specific amplification based on the aimed nucleotide sequence is known to those skilled in the art (Current Protocols in Molecular Biology, Ausubel et al. edit, (1987) John Wiley & Sons, Section 6.1-6.4). In designing a primer based on the 5'-end sequence, the primer is designed so as that, in principle, the amplification products will include the translation start site. Accordingly, for example, when the 5'-end primer is designed based on the nucleotide sequence of 5' untranslated region (5'UTR), any part of the 5'-end, which ensures the specificity to the cDNA of interest, can be selected as the primer.

When synthesizing a full-length cDNA, the target nucleotide sequence to be amplified can extend to several thousand bp in some cDNA. However, it is possible to amplify such a long nucleotides by using such as LA PCR (Long and Accurate PCR). It is advantageous to use LA PCR when synthesizing long DNA. In LA PCR, in which a special DNA polymerase having 3'->5' exonuclease activity is used, misincorporated nucleotides can be removed. Accordingly, accurate synthesis of the complementary strand can be achieved even with a long nucleotide sequence. By using LA PCR, it is reported that amplification of a nucleotide with 20 kb longer can be achieved under desirable conditions (Takeshi Hayashi (1996) Jikken-Igaku Bessatsu, "Advanced Technologies in PCR" Youdo-sha).

A template DNA for synthesizing the full-length cDNA of the present invention can be obtained by using cDNA libraries that are prepared by various methods. The full-length cDNA clones of the present invention are clones with high probability of completeness in length, which were obtained by the method comprising the steps of [1] preparing libraries containing cDNAs with the very high fullness ratio by oligo-capping, and [2] assembling the 5'-end sequences and selecting one with the highest probability of completeness in length in the cluster formed (there are many clones longer in the 5'-end direction).

However, the uses of primers designed based on the full-length nucleotide sequences provided by the present invention enable easily obtaining full-length cDNAs without such a special technique.

The problem with the cDNA libraries prepared by the known methods or commercially available is that mRNA contained in the libraries has very low fullness ratio. Thus, it is difficult to screen full-length cDNA clone directly from the library using ordinary cloning methods. The present invention has revealed a nucleotide sequence of novel full-length cDNA. If a full-length nucleotide sequence is provided, it is possible to synthesize a target full-length cDNA by using enzymatic reactions such as PCR. In particular, a full-length-enriched cDNA library, synthesized by methods such as oligo-capping, is desirable to synthesize a full-length cDNA with more reliability.

The 5'-end sequence of the full-length cDNA clones of the invention can be used to isolate the regulatory element of transcription including the promoter on the genome. A rough draft of the human genome (analysis of human genomic sequence with lower accuracy), which covers 90% of the genome, has been reported (Nature, Vol. 409, 814-823, 2001), and by the year 2003, analysis of the entire human genomic sequence is going to be finished. However, it is hard to analyze with software the transcription start sites on the human genome, in which long introns exist. By contrast, it is easy to specify the transcription start site on the genomic sequence using the nucleotide sequence which includes the 5'-end of the full-length cDNA clone of the present invention, and thus it is easy to obtain the genomic region involved in transcription regulation, which includes the promoter that is contained in the upstream of the transcription start site.

The polypeptide encoded by the full-length cDNA of the invention can be prepared as a recombinant polypeptide or as a natural polypeptide. For example, the recombinant polypeptide can be prepared by inserting the polynucleotide encoding the polypeptide of the invention into a vector, introducing the vector into an appropriate host cell and purifying the polypeptide expressed within the transformed host cell, as described below. In contrast, the natural polypeptide can be prepared, for example, by utilizing an affinity column to which an antibody against the polypeptide of the invention (Current Protocols in Molecular Biology (1987) Ausubel et al. edit, John Wiley & Sons, Section 16.1-16.19) is attached. The antibody used for affinity purification may be either a polyclonal antibody, or a monoclonal antibody. Alternatively, in vitro translation (See, for example, "On the fidelity of mRNA translation in the nuclease-treated rabbit reticulocyte lysate system." Dasso M. C., and Jackson R. J. (1989) Nucleic Acids Res. 17: 3129-3144) may be used for preparing the polypeptide of the invention.

Polypeptides functionally equivalent to the polypeptides of the present invention can be prepared based on the activities, which were clarified in the above-mentioned manner, of the polypeptides of the present invention. Using the biological activity possessed by the polypeptide of the invention as an index, it is possible to verify whether or not a particular polypeptide is functionally equivalent to the polypeptide of the invention by examining whether or not the polypeptide has said activity.

Polypeptides functionally equivalent to the polypeptides of the present invention can be prepared by those skilled in the art, for example, by using a method for introducing mutations into an amino acid sequence of a polypeptide (for example, site-directed mutagenesis (Current Protocols in Molecular Biology, edit, Ausubel et al., (1987) John Wiley & Sons, Section 8.1-8.5) Besides, such polypeptides can be generated by spontaneous mutations. The present invention also includes a polypeptide comprising the amino acid sequence shown in Table 1 in which one or more amino acids are substituted, deleted, inserted, and/or added, as long as the polypeptides have the equivalent functions to those of the polypeptides identified in the present Examples described later.

There are no limitations on the number and sites of amino acid mutations, as long as the polypeptides maintain the functions thereof. The number of mutations typically corresponds to 30% or less, or 20% or less, or 10% or less, preferably 5% or less, or 3% or less of the total amino acids, more preferably 2% or less or 1% or less of the total amino acids. Alternatively, herein, substitution of one or more amino acids includes substitution of several amino acids. As used herein, the term "several amino acids" means, for example, 5 amino acids, preferably 4 or 3 amino acids, more preferably 2 amino acids, and further preferably 1 amino acid.

From the viewpoint of maintaining the polypeptide function, it is preferable that a substituted amino acid has a similar property to that of the original amino acid. For example, Ala, Val, Leu, Ile, Pro, Met, Phe and Trp are assumed to have similar properties to one another because they are all classified into a group of non-polar amino acids. Similarly, substitution can be performed among non-charged amino acid such as Gly, Ser, Thr, Cys, Tyr, Asn, and Gln, acidic amino acids such as Asp and Glu, and basic amino acids such as Lys, Arg, and His.

In addition, polypeptides functionally equivalent to the polypeptides of the present invention can be isolated by using techniques of hybridization or gene amplification known to those skilled in the art. Specifically, using the hybridization technique (Current Protocols in Molecular Biology, edit, Ausubel et al., (1987) John Wiley & Sons, Section 6.3-6.4)), those skilled in the art can usually isolate a polynucleotide highly homologous to the polynucleotide encoding the polypeptide identified in the present Example based on the identified nucleotide sequence (Table 1) or a portion thereof and obtain the functionally equivalent polypeptide from the isolated polynucleotide. The present invention include polypeptides encoded by the polynucleotides hybridizing with the polynucleotides encoding the polypeptides identified in the present Example, as long as the polypeptides are functionally equivalent to the polypeptides identified in the present Example. Organisms from which the functionally equivalent polypeptides are isolated are illustrated by vertebrates such as human, mouse, rat, rabbit, pig and bovine, but are not limited to these animals.

Washing conditions of hybridization for the isolation of polynucleotides encoding the functionally equivalent polypeptides are usually "1×SSC, 0.1% SDS, 37° C."; more stringent conditions are "0.5×SSC, 0.1% SDS, 42° C."; and still more stringent conditions are "0.1×ssc, 0.1% SDS, 65° C.". Alternatively, the following conditions can be given as hybridization conditions of the present invention. Namely, conditions in which the hybridization is done at "6×SSC, 40% Formamide, 25° C.", and the washing at "1×SSC, 55° C." can be given. More preferable conditions are those in which the hybridization is done at "6×SSC, 40% Formamide, 37° C.", and the washing at "0.2×SSC, 55° C.". Even more preferable are those in which the hybridization is done at "6×SSC, 50% Formamide, 37° C.", and the washing at "0.1×SSC, 62° C.". The more stringent the conditions of hybridization are, the more frequently the polynucleotides highly homologous to the probe sequence are isolated. Therefore, it is preferable to conduct hybridization under stringent conditions. Examples of stringent conditions in the present invention are, washing conditions of "0.5×SSC, 0.1% SDS, 42° C.", or alternatively, hybridization conditions of "6×SSC, 40% Formamide, 37° C.", and the washing at "0.2×SSC, 55° C.".

One skilled in the art can suitably select various conditions, such as dilution ratios of SSC, formamide concentrations, and temperatures to accomplish a similar stringency.

However, the above-mentioned combinations of SSC, SDS and temperature conditions are indicated just as examples. Those skilled in the art can select the hybridization conditions with similar stringency to those mentioned above by properly combining the above-mentioned or other factors (for example, probe concentration, probe length and duration of hybridization reaction) that determines the stringency of hybridization.

The amino acid sequences of polypeptides isolated by using the hybridization techniques usually have high identity to those of the polypeptides of the present invention, which are shown in Table 1. The present invention encompasses a polynucleotide comprising a nucleotide sequence that has a high identity to the nucleotide sequence of claim 1 (a). Furthermore, the present invention encompasses a peptide, or polypeptide comprising an amino acid sequence that has a high identity to the amino acid sequence encoded by the polynucleotide of claim 1 (b). The term "high identity" indicates sequence identity of at least 40% or more; preferably 60% or more; and more preferably 70% or more. Alternatively, more preferable is identity of 90% or more, or 93% or more, or 95% or more, furthermore, 97% or more, or 99% or more. The identity can be determined by using the BLAST search algorithm.

As used herein, "percent identity" of amino acid sequences or nucleic acids is determined using the algorithm BLAST of Karlin and Altschul (Proc. Natl. Acad. Sci. USA 90:5873-5877, 1993). Such an algorithm is incorporated into the BLASTN and BLASTX programs of Altschul et al. (J. Mol. Biol. 215:403-410, 1990). BLAST nucleotide searches are performed with the BLASTN program, for example, score=100, wordlength=12. BLAST protein searches are performed with the BLASTX program, for example, score=50, wordlength=3. When utilizing BLAST and Gapped BLAST programs, the default parameters of the respective programs are used. Avalible on the world wide web at ncbi.nlm.nih.gov.

With the gene amplification technique (PCR) (Current Protocols in Molecular Biology, edit, Ausubel et al., (1987) John Wiley & Sons, Section 6.1-6.4)) using primers designed based on the nucleotide sequence (Table 1) or a portion thereof identified in the present Example, it is possible to isolate a polynucleotide fragment highly homologous to the polynucleotide sequence or a portion thereof and to obtain functionally equivalent polypeptide to a particular polypeptide identified in the present Example based on the isolated polynucleotide fragment.

The present invention also provides a polynucleotide containing at least 15 nucleotides complementary to a polynucleotide comprising a nucleotide sequence of SEQ ID NOs shown in Table 1 or the complementary strand thereof. Herein, the term "complementary strand" is defined as one strand of a double strand DNA composed of A:T and G:C base pair to the other strand. Also, "complementary" is defined as not only those completely matching within a continuous region of at least 15 nucleotides, but also having a identity of at least 70%, favorably 80% or higher, more favorably 90% or higher, and most favorably 95% or higher within that region. The identity may be determined using the algorithm described herein.

Such a polynucleotide includes probes and primers used for the detection and amplification of a polynucleotide encoding the inventive polypeptide. When used as a primer, the polynucleotide usually comprises 15 to 100 bp, and preferably of 15 to 35 bp. When used as a probe, the polynucleotide comprises the whole or a part of the sequence of a polynucleotide of the invention, and comprises at least 15 bp. When used as primers, such polynucleotides are complementary at the 3'-end, and restriction enzyme recognition sequences or tags can be added to the 5'-end.

Furthermore, polynucleotides of the present invention include an antisense polynucleotide for suppressing the expression of a polypeptide of the invention, which comprises an amino acid sequence of SEQ ID NOs shown in Table 1. To exert an antisense effect, an antisense polynucleotide has at least 15 bp or more, for example 50 bp or more, preferably 100 bp or more, and more preferably 500 bp or more, and usually has 3000 bp or less, and preferably 2000 bp or less. Antisense polynucleotides can be used in the gene therapy of diseases caused by abnormalities of the polypeptides of the invention (abnormal function or abnormal expression). An antisense polynucleotide can be prepared, for example, by the phosphorothioate method ("Physicochemical properties of phosphorothioate oligodeoxynucleotides." Stein (1988) Nucleic Acids Res. 16: 3209-3221) based on the sequence information of polynucleotide encoding a polypeptide of the invention (for example, the nucleotide sequence of SEQ ID NO: 1).

The polynucleotides or antisense polynucleotides of the present invention can be used in, for example, gene therapy. As target diseases, for example, cancers or various inflammatory diseases may be preferable. These molecules can be used for gene therapy, for example, by administrating them to patients by the in vivo or ex vivo method using virus vectors such as retrovirus vectors, adenovirus vectors, and adeno-related virus vectors, or non-virus vectors such as liposomes.

The present invention also includes a partial peptide of the polypeptides of the invention. The partial peptide comprises a polypeptide generated as a result that a signal peptide has been removed from a secretory protein. If the polypeptide of the present invention has an activity as a receptor or a ligand, the partial peptide may function as a competitive inhibitor of the polypeptide and may bind to the receptor (or ligand). In addition, the present invention includes an antigen peptide for raising antibodies. For the peptides to be specific for the polypeptide of the invention, the peptides comprise at least 7 amino acids, preferably 8 amino acids or more, more preferably 9 amino acids or more, and even more preferably 10 amino acids or more. The peptide can be used for preparing antibodies against the polypeptide of the invention, or competitive inhibitors of them, and also screening for a receptor that binds to the polypeptide of the invention. The partial peptides of the invention can be produced, for example, by genetic engineering methods, known methods for synthesizing peptides, or digesting the polypeptide of the invention with an appropriate peptidase.

The present invention also relates to a vector into which a polynucleotide of the invention is inserted. The vector of the invention is not limited as long as it contains the inserted polynucleotide stably. For example, if E. coli is used as a host, vectors such as pBluescript vector (Stratagene) are preferable as a cloning vector. To produce the polypeptide of the invention, expression vectors are especially useful. Any expression vector can be used as long as it is capable of expressing the polypeptide in vitro, in E. coli, in cultured cells, or in vivo.

For example, pBEST vector (Promega) is preferable for in vitro expression, pET vector (Invitrogen) for E. coli, pME18S-FL3 vector (GenBank Accession No. AB009864) for cultured cells, and pME18S vector (Mol. Cell. Biol. (1988) δ: 466-472) for in vivo expression. To insert the polynucleotide of the invention, ligation utilizing restriction sites can be performed according to the standard method (Current Protocols in Molecular Biology (1987) Ausubel et al. edit, John Wiley & Sons, Section 11.4-11.11).

Recently, the technique of GATEWAY™ system (Invitrogen), which is an expression vector construction system for polypeptide expression, has been developed (Experimental Medicine, Vol. 18, No. 19 (December), p2716-2717, 2000). This system includes two types of site-specific recombinases (BP CLONASE™ and LR CLONASE™) derived from lambda phage and uses BP CLONASE™-specific recombination sites for an Entry Vector and LR CLONASE™-specific recombination sites for a Destination Vector, which may comprise a tag useful for polypeptide purification. With this system, an expression vector can be obtained by using homologous recombination.

First, a polynucleotide fragment of interest is inserted into the entry vector using the first recombination. Then, the secondary recombination is allowed to take place between the entry vector, where the polynucleotide fragment of interest has been inserted, and the destination vector. Thus, the expression vector can be prepared rapidly and highly efficiently. With the abovementioned typical method using restriction enzyme and ligase reactions, the step of expression vector construction and expression of polypeptide of interest takes about 7 to 10 days. However, with the GATEWAY™ system, the polypeptide of interest can be expressed and prepared in only 3 to 4 days. Thus, the system ensures a high-throughput functional analysis for expressed polypeptides (avalible on the world wide web at biotech.nikkeibp.co.jp/netlink/lto/gateway/).

The present invention also relates to a transformant carrying the vector of the invention. Any cell can be used as a host into which the vector of the invention is inserted, and various kinds of host cells can be used depending on the purposes. For strong expression of the polypeptide in eukaryotic cells, COS cells or CHO cells can be used, for example.

Introduction of the vector into host cells can be performed, for example, by calcium phosphate precipitation method, electroporation method (Current Protocols in Molecular Biology (1987) Ausubel et al. edit, John Wiley & Sons, Section 9.1-9.9), lipofectamine method (GIBCO-BRL), or microinjection method, etc.

Further, a polynucleotide containing at least 15 nucleotides comprising a nucleotide sequence of any one of the polynucleotides comprising the nucleotide sequences of SEQ ID NOs shown in Table 1 or the complementary strand thereof can be used not only as a primer for synthesizing full-length cDNAs but also for testing and diagnosing the abnormalities of the polypeptide encoded by the full-length cDNA of the present invention. For example, by utilizing polymerase chain reaction (genomic DNA-PCR, or RT-PCR) using the polynucleotide of the invention as a primer, polynucleotide encoding the polypeptide of the invention can be amplified. It is also possible to obtain the regulatory region of expression in the 5'-upstream by using PCR or hybridization since the transcription start site within the genomic sequence can be easily specified based on the 5'-end sequence of the full-length cDNA. The obtained genomic region can be used for detection and/or diagnosis of the abnormality of the sequence by RFLP analysis, SSCP, or sequencing. Especially, in the case where expression of the mRNA of the present invention varies according to a specific disease, analysis of the amount of expression of the mRNA using the polynucleotide of the present invention as a probe or a primer enables detection and diagnosis of the disease.

The present invention also relates to antibodies that bind to the polypeptide of the invention. There are no limitations in the form of the antibodies of the invention. They include polyclonal antibodies, monoclonal antibodies, or their portions that can bind to an antigen. They also include antibodies of all classes. Furthermore, special antibodies such as humanized antibodies and chimeric antibodies are also included.

The polyclonal antibody of the invention can be obtained according to the standard method by synthesizing an oligopeptide corresponding to the amino acid sequence and immunizing rabbits with the peptide (Current Protocols in Molecular Biology (1987) Ausubel et al. edit, John Wiley & Sons, Section 11.12-11.13). The monoclonal antibody of the invention can be obtained according to the standard method by purifying the polypeptide expressed in E. coli, immunizing mice with the polypeptide, and producing a hybridoma cell by fusing the spleen cells and myeloma cells (Current Protocols in Molecular Biology (1987) Ausubel et al. edit, John Wiley & Sons, Section 11.4-11.11).

The antibody binding to the polypeptide of the present invention can be used for purification of the polypeptide of the invention, and also for detection and/or diagnosis of the abnormalities of the expression and structure of the polypeptide. Specifically, polypeptides can be extracted, for example, from tissues, blood, or cells, and the polypeptide of the invention is detected by Western blotting, immunoprecipitation, or ELISA, etc. for the above purpose.

Furthermore, the antibody binding to the polypeptide of the present invention can be utilized for treating the diseases that associates with the polypeptide of the invention. If the antibodies are used for treating patients, human antibodies, humanized antibodies, or chimeric antibodies are preferable in terms of their low antigenicity. The human antibodies can be prepared by immunizing a mouse whose immune system is replaced with that of human (e.g., see "Functional transplant of megabase human immunoglobulin loci recapitulates human antibody response in mice" Mendez, M. J. et al. (1997) Nat. Genet. 15: 146-156). The humanized antibodies can be prepared by recombination of the hypervariable region of a monoclonal antibody (Methods in Enzymology (1991) 203: 99-121).

A cDNA of the present invention encodes, for example, an amino acid sequence of a protein that is predicted to have the following function. The use of the amino acid sequences of the polypeptides encoded by the cDNAs of the present invention enables predicting that the polypeptides have the following functions. It can be predict, from the results of homology search of SwissProt, GenBank, UniGene, or nr, that these polypeptides have such functions. Specifically, for instance, as shown in Examples, searching for a known gene or polypeptide that is homologous to the partial sequence of the full-length cDNA of the invention and referring the function of the gene and of the polypeptide encoded by the gene make it possible to predict the function of the polypeptide encoded by the cDNA of the invention. In this way, each of 1216 clones out of the 2443 full-length cDNA clones of the invention was predicted to encode a polypeptide that was classified into the following categories.

Secretory and/or membrane protein (632 clones)
    Glycoprotein-related protein (128 clones)
    Signal transduction-related protein (84 clones)
    Transcription-related protein (144 clones)
    Disease-related protein (387 clones)
    Enzyme and/or metabolism-related protein (206 clones)
    Cell division- and/or cell proliferation-related protein (33 clones)
    Cytoskeleton-related protein (75 clones)
    Nuclear protein and/or RNA synthesis-related protein (65 clones)
    Protein synthesis- and/or transport-related protein (62 clones)
    Cellular defense-related protein (15 clones)
    Development and/or differentiation-related protein (13 clones)
    DNA- and/or RNA-binding protein (174 clones)
    ATP- and/or GTP-binding protein (68 clones)

The functions of the polypeptides encoded by the cDNAs of the present invention can be predicted by assessing the presence of signal sequence, transmembrane region, nuclear translocation signal, glycosylation signal, phosphorylation site, and zinc finger motif, SH3 domain, etc. in the amino acid sequences. The programs, PSORT (Nakai K., and Kanehisa M. (1992) Genomics 14: 897-911), SOSUI (Hirokawa T. et al. (1998) Bioinformatics 14: 378-379) (Mitsui Knowledge Industry), and MEMSAT (Jones D. T., Taylor W. R., and Thornton J. M. (1994) Biochemistry 33: 3038-3049) can be used to predict the existence of the signal sequence or transmembrane region. Alternatively, a partial amino acid sequence of the polypeptide is fused with another polypeptide such as GFP, the fusion polypeptide is transfected into cultured cells, and the localization is analyzed to predict the function of the original polypeptide.

Based on the determined nucleotide sequences of the full-length cDNAs obtained in the present invention, it is possible to predict more detailed functions of the polypeptides encoded by the cDNA clones, for example, by searching the databases such as GenBank, Swiss-Prot, UniGene, and nr for homologies of the cDNAs; or by searching the amino acid sequences deduced from the full-length cDNAs for signal sequences by using software programs such as PSORT, for transmembrane regions by using software programs such as SOSUI or for motifs by using software programs such as Pfam (avalible on the world wide web at sanger.ac.uk/Software/Pfam/index.shtml) and PROSITE (avalible on the world wide web at expasy.ch/prosite/). As a matter of course, the functions are often predictable by using partial sequence information (preferably 300 nucleotides or more) instead of the full-length nucleotide sequences. However, the result of the prediction by using partial nucleotide sequence does not always agree with the result obtained by using full-length nucleotide sequence, and thus, it is needless to say that the prediction of function is preferably performed based on the full-length nucleotide sequences.

GenBank, Swiss-Prot, UniGene and nr databases were searched for homologies of the full-length nucleotide sequences of the 2443 clones (see Example 6). The amino acid sequences deduced from the full-length nucleotide sequences were searched for functional domains by PSORT, SOSUI and Pfam. Prediction of functions of polypeptides encoded by the clones and the categorization thereof were performed based on these results obtained. The categorization was carried out by the following method.

[1] Firstly, the cDNA clones were classified into the above-mentioned 14 functional categories based on the results of annotation-based categorization (using the keywords in the case of Swiss-Prot hit data; using Definition or Reference information in the case of GenBank, UniGene, or nr hit data), and the signal sequence search of the deduced ORFs by PSORT and the transmembrane region search by SOSUI.

[2] Secondly, clones which had been unassignable to the categories by the method of [1] were searched for functional domains and/or motifs by Pfam. Based on the results, the clones were additionally classified into the above-mentioned 14 types of categories when they had a functional domain and/or motif assignable to any one of the categories.

HEART20049410 was identified as one of 632 clones presumably belonging to the category of secretory and/or membrane proteins.

HEART20049410 was also identified as one of 387 clones presumably belonging to the category of disease-related proteins.

A polypeptide does not always belong solely to a single category of the above-described functional categories, and therefore, a polypeptide may belong to any of the predicted functional categories. Besides, additional functions can be found for the clones classified into these functional categories by further analyses.

Since the polypeptide encoded by clones of the invention contains full-length amino acid sequence, it is possible to analyze its biological activity, and its effect on cellular conditions such as cell proliferation and differentiation by expressing the polypeptide as a recombinant polypeptide using an appropriate expression system, injecting the recombinant into the cell, or raising a specific antibody against the polypeptide.

The biological activities of respective polypeptides can be analyzed by the methods as shown below.

Secretory protein, transmembrane protein:
    "Ion Channels" (Ed., R. H. Ashley, 1995) of "The Practical Approach Series" (IRL PRESS),
    "Growth Factors" (Eds., I. McKay, I. Leigh, 1993),
    "Extracellular Matrix" (Eds., M. A. Haralson, J. R. Hassell, 1995);

Glycoprotein-related protein:
    "Glycobiology" (Eds., M. Fukuda, A. Kobata, 1993) of "The Practical Approach Series" (IRL PRESS),
    "Glycoprotein Analysis in Biomedicine" (Ed., Elizabeth F. Hounsell, 1993) of "Method in Molecular Biology" (Humana Press) series;

Signal transduction-related protein:
    "Signal Transduction" (Ed., G. Milligan, 1992) of "The Practical Approach Series" (IRL PRESS),
    "Protein Phosphorylation" (Ed., D. G. Hardie, 1993), or
    "Signal Transduction Protocols" (Eds., David A. Kendall, Stephen J. Hill, 1995) of "Method in Molecular Biology" (Humana Press) series;

Transcription-related protein:
"Gene Transcription" (Eds., B. D. Hames, S. J. Higgins, 1993) of "The Practical Approach Series" (IRL PRESS),
"Transcription Factors" (Ed., D. S. Latchman, 1993);
Enzyme and/or metabolism-related protein:
"Enzyme Assays" (Eds., ROBERT EISENTHAL and MICHAEL J. DANSON, 1992) of "The Practical Approach Series" (IRL PRESS);
Cell division and/or cell proliferation-related protein:
"Cell Growth, Differentiation and Senescence" (Ed., GEORGE STUDZINSKI, 2000) of "The Practical Approach Series" (IRL PRESS);
Cytoskeleton-related protein:
"Cytoskeleton: Signalling and Cell Regulation" (Eds., KERMIT L. CARRAWAY and CAROLIE A. CAROTHERS CARRAWAY, 2000) of "The Practical Approach Series" (IRL PRESS),
"Cytoskeleton Methods and Protocols" (Ed., Gavin, Ray H., 2000) of "Method in Molecular Biology" (Humana Press) series;
Nuclear protein and/or RNA synthesis-related protein:
"Nuclear Receptors" (Ed., DIDIER PICARD, 1999) of "The Practical Approach Series" (IRL PRESS),
"RNA Processing" (Eds., STEPHEN J. HIGGINS and B. DAVID HAMES, 1994);
Protein synthesis and/or transport-related protein:
"Membrane Transport" (Ed., STEPHEN A. BALDWIN, 2000) of "The Practical Approach Series" (IRL PRESS),
"Protein Synthesis Methods and Protocols" (Eds., Martin, Robin, 1998) of "Method in Molecular Biology" (Humana Press) series;
Cellular defense-related protein:
"DNA Repair Protocols" (Henderson, Daryl S., 1999) of "Method in Molecular Biology" (Humana Press) series,
"Chaperonin Protocols" (Eds., Schneider, Christine, 2000);
Development and/or differentiation-related protein:
"Developmental Biology Protocols" (Eds., ROBERT EISENTHAL and MICHAEL J. DANSON, 1992) of "Method in Molecular Biology" (Humana Press) series;
DNA- and/or RNA-binding protein:
"DNA-Protein Interactions Principles and Protocols" (Eds., Kneale, G. Geoff, 1994) of "Method in Molecular Biology" (Humana Press) series,
"RNA-Protein Interaction Protocols" (Eds., Haynes, Susan R., 1999);
ATP- and/or GTP-binding protein:
"Signal Transduction Protocols" (Eds., David A. Kendall, Stephen J. Hill, 1995) of "Method in Molecular Biology" (Humana Press) series.

In the categorization, the clone predicted to belong to the category of secretory and/or membrane protein means a clone having hit data with some annotation, such as growth factor, cytokine, hormone, signal, transmembrane, membrane, extracellular matrix, receptor, G-protein coupled receptor, ionic channel, voltage-gated channel, calcium channel, cell adhesion, collagen, connective tissue, etc., suggesting that it was a secretory or membrane protein, or a clone in which the presence of nucleotide sequence encoding a signal sequence or transmembrane region was suggested by the results of PSORT and SOSUI analyses for deduced ORF.

The clone predicted to belong to the category of glycoprotein-related protein means a clone having hit data with some annotation, such as glycoprotein, suggesting that the clone encodes a glycoprotein-related protein.

The clone predicted to belong to the category of signal transduction-related protein means a clone having hit data with some annotation, such as serine/threonine-protein kinase, tyrosine-protein kinase, SH3 domain, SH2 domain, etc., suggesting that the clone encodes a signal transduction-related protein.

The clone predicted to belong to the category of transcription-related protein means a clone having hit data with some annotation, such as transcription regulation, zinc finger, homeobox, etc., suggesting that the clone encodes a transcription-related protein.

The clone predicted to belong to the category of disease-related protein means a clone having hit data with some annotation, such as disease mutation, syndrome, etc., suggesting that the clone encodes a disease-related protein, or a clone whose full-length nucleotide sequence has hit data for Swiss-Prot, GenBank, UniGene, or nr, where the hit data corresponds to genes or polypeptides which have been deposited in the Online Mendelian Inheritance in Man (OMIM) (avalible on the world wide web at ncbi.nlm.nih.gov/Omim/), which is the human gene and disease database described later.

The clone predicted to belong to the category of enzyme and/or metabolism-related protein means a clone having hit data with some annotation, such as metabolism, oxidoreductase, E. C. No. (Enzyme commission number), etc., suggesting that the clone encodes an enzyme and/or metabolism-related protein.

The clone predicted to belong to the category of cell division and/or cell proliferation-related protein means a clone having hit data with some annotation, such as cell division, cell cycle, mitosis, chromosomal protein, cell growth, apoptosis, etc., suggesting that the clone encodes a cell division and/or cell proliferation-related protein.

The clone predicted to belong to the category of cytoskeleton-related protein means a clone having hit data with some annotation, such as structural protein, cytoskeleton, actin-binding, microtubles, etc., suggesting that the clone encodes a cytoskeleton-related protein.

The clone predicted to belong to the category of nuclear protein and/or RNA synthesis-related protein means a clone having hit data with some annotation, such as nuclear protein, RNA splicing, RNA processing, RNA helicase, polyadenylation, etc., suggesting that the clone encodes a nuclear protein and/or RNA synthesis-related protein.

The clone predicted to belong to the category of protein synthesis and/or transport-related protein means a clone having hit data with some annotation, such as translation regulation, protein biosynthesis, amino-acid biosynthesis, ribosomal protein, protein transport, signal recognition particle, etc., suggesting that the clone encodes a protein synthesis and/or transport-related protein.

The clone predicted to belong to the category of cellular defense-related protein means a clone having hit data with some annotation, such as heat shock, DNA repair, DNA damage, etc., suggesting that the clone encodes a cellular defense-related protein.

The clone predicted to belong to the category of development and/or differentiation-related proteins means a clone having hit data with some annotation, such as developmental protein, etc., suggesting that the clone encodes a development and/or differentiation-related protein.

The clone predicted to belong to the category of DNA- and/or RNA-binding protein means a clone having hit data with some annotation, such as DNA-binding, RNA-binding, etc.

The clone predicted to belong to the category of ATP- and/or GTP-binding protein means a clone having hit data with some annotation, such as ATP-binding, GTP-binding, etc.

As to a protein involved in a disease, it is possible to perform a functional analysis as described above, but also possible to analyze correlation between the expression or the activity of the protein and a certain disease by using a specific antibody that is obtained by using expressed protein. Alternatively, it is possible to utilize the database OMIM, which is a database of human genes and diseases, to analyze the protein. Further, new information is constantly being deposited in the OMIM database. Therefore, it is possible for one skilled in the art to find a new relationship between a particular disease and a gene of the present invention in the most up-to-date database. The proteins involved in diseases are useful for developing a diagnostic marker or medicines for regulation of their expression and activity, or as a target of gene therapy.

Also, as for a secretory protein, membrane protein, signal transduction-related protein, glycoprotein-related protein, or transcription-related protein, etc., search of the OMIM with the following keywords resulted in the finding that the proteins are involved in many diseases (the result of the OMIM search for secrete and membrane proteins is shown below). Also, association between proteins related to signal transduction or transcription and diseases is reported in "Transcription Factor Research-1999" (Fujii, Tamura, Morohashi, Kageyama, and Satake edit, (1999) Jikken-Igaku Zoukan, Vol. 17, No. 3), and "Gene Medicine" (1999) Vol. 3, No. 2). When cancer is used as an example, as described in "Biology of Cancer" (S. Matsubara, 1992) of Life Science series (Shokabo), many proteins are involved in cancers, which include enzyme and/or metabolism-related proteins, cytoskeleton-related proteins, cell division and/or cell proliferation-related proteins as well as secretory proteins, membrane proteins, signal transduction-related proteins, glycoprotein-related proteins, transcription-related proteins. As clearly seen by the above example, it is evident that not only disease-related proteins but also secretory proteins, membrane proteins, signal transduction-related proteins, glycoprotein-related proteins, transcription-related proteins, etc. are often involved in diseases, and thus they can be useful targets in the field of medical industry.

The result of the OMIM search for secretory and membrane proteins is shown below, in which the keywords,
 (1) secretion protein,
 (2) membrane protein,
 (3) channel, and
 (4) extracellular matrix were used.

Shown in the search result are only the accession numbers in the OMIM. Using the number, data showing the relationship between a disease and a gene or protein can be seen. The OMIM data has been renewed everyday.

1) Secretion Protein 354 entries found, searching for "secretion protein"

*604667, *104760, *176860, *151675, *139320, *107400, *604029, *118910, #200100, *176880, *603850, *147572, *604028, *179513, *125950, *139250, *246700, *600946, *600560, *602926, 185860, *605083, *603215, *602421, *157147, *179512, *600174, *109270, *604710, *138120, *179510, *600998, *179509, *170280, *179511, *600626, *603831, *601489, *154545, *179490, *603826, *122559, *603216, *102720, *147290, *164160, *603062, *112262, *602672, *605435, *605322, *131230, *601652, *603166, *601746, *601591, *179508, #160900, *104311, *600759, *147545, *167805, #104300, *167770, #219700, *168470, *601684, *602049, *601146, *605227, *602434, *602534, *114840, *603489, *604323, *107470, *600753, *600768, *118825, *600564, *604252, *173120, *134370, *192340, *308230, *600322, *605359, *600046, *300090, 106160, *600041, #262500, *605563, *150390, *158106, *182590, #103580, *104610, #173900, *134797, *143890, #145980, *306900, *308700, *176300, *227500, *137350, *154700, *138079, *600760, *107730, *142410, *147670, *124092, *590050, *152760, *600509, *605646, *201910, *227600, *152790, *300200, *300300, 300800, *138160, *107741, *120150, *601199, *120180, *120160, *176730, *133170, *122560, *107300, *137241, *120140, *101000, *193400, *217000, *272800, *600937, #201710, *600377, #174800, *106100, #274600, *173350, #177170, *147620, *214500, *131244, *202110, *120120, *601007, *191160, *147470, *603372, *600733, *252800, *190160, *138040, *158070, *162151, #125700, #130070, *113811, *603355, *171060, *136435, #184700, *603732, *190180, *164008, *186590, *120220, *604312, *152200, *138130, *605085, *605353, *600840, #166210, *188545, *207750, *173360, *601933, #194050, *153450, *138850, *253200, *307030, *157145, *600514, *600262, *264080, *147380, *600281, #204000, #227810, *232200, *188826, *232800, *161561, #166200, *188400, *153620, *182099, *218040, #265800, *172400, #177200, *176805, #211600, *214700, #176410, *152780, *600633, *601771, *301500, *605402, *601922, *307800, *147892, *147720, *312060, #520000, *147660, *106150, *602358, *107270, *601769, *147440, *604558, *131530, *600270, *601610, *603692, *603401, *600423, *601604, *603345, #125853, *602843, *142640, *603044, *605740, *134830, *602779, *130660, *139191, *137035, *600761, *601340, *600823, *107740, *130160, *600877, *605110, *600945, *130080, *600957, #130050, *605580, *118444, *601124, *124020, 122470, *120700, *603201, *137216, *601185, *138945, *218030, *600839, #240600, #262400, #162300, *162330, *188450, #265850, *263200, *162641, *300159, *601038, #191390, *201810, *601398, *602384, *131240, *602423, *139392, *142703, *602663, *232700, *602682, #602722, *602730, *600734, *188540, *182452, *601538, *603061, *146880, *603140, *603160, *142704, #252650, *182280, *125255, *603252, #131750, *182139, *182100, #259420, #261100, *603493, *601745, *182098, *603795, *123812, *600264, *147940, *180246, *180245, *118888, #604284, *168450, *118455, *604398, *604433, *601919, *118445, *600031, *604961, *605032, *605033, *171050, #171300, *131243, *109160, *605254, 274900, #171400, *600042, *151670, *184600, *605470, *605546, *176760, *602008, *102200, *605720, *600732, *605901

2) Membrane Protein 1489 entries found, searching for "membrane protein"

*130500, *605704, *305360, *153330, *173610, *109270, *170995, *170993, *104776, *602333, *309060, *605703, *120920, *605943, *602690, *159430, *600897, *133090, *601178, *602413, *602003, *604405, *605940, *603237, *109280, *600378, *602173, *107776, *602334, *602335, *125305, *601134, *309845, *605731, *154045, *603241, *603718, *600594, *603214, *185881, *603657, *600182, *603177, *605331, *601476, *605456, *601114, *605190, *600723, *603904, *136950, *300222, *602879, *185880, *605348, *300096, *602257, *177070, *310200, *603062, *603344, *600039, *602977, *300100, *128240, *600959, *600322, *227400, *186945, *600946, *602534, *602048, *182900, *601097, *600267, *602625, *136430, *602421, *601047, *107450, *143450, *603141, *184756, *164730, *159440, *154050, *600579, *312080, *604202, *603700, *600447, *256540, *604691, *158343, *600403, *602414, *137290, *176640, *176981, *600179, *600754, *604456, *604693, *605875, *604605, *188860, *300172, *602910, *604323, *219800, *601848, *603179, *600279, *602251, #222700, *603831, *605072, *605377, *601028, *604155,

*108733, *104225, *601896, *601510, *173335, *107770, *601767, *600046, *603850, *600040, *603784, *603234, 188560, *605863, *121015, *605862, *605861, *186946, *604252, *603215, *142461, *604597, *603143, *605264, *603735, *176860, *605536, *176801, *180721, *603355, *104760, *131560, *310300, *602631, *304700, #309400, *603142, *143890, *605431, *600753, *115501, *176790, *600266, *601691, *168468, *601239, *602216, #104300, *605613, *601595, *605550, *125950, *605475, *602217, *602261, *603534, *602262, *604631, *190315, *601313, *604306, *104311, *604672, *605000, *602461, *605548, *602296, *604376, *121014, *121011, *600691, *604262, *139310, *304040, *605445, *179514, *179512, *151460, #160900, *120130, *128239, *601158, *601403, *176943, *601014, 300800, *300294, *601757, *185470, *273800, *605034, *602887, #185000, *604871, *603593, *603583, *605454, *104775, *605872, *141180, *602713, *603531, *139150, *601531, *601832, *605452, *134651, *604156, *120620, *605883, *604142, *166945, *605324, *600816, *604699, *300112, *605182, *600164, *182180, *605071, *300023, *605057, *308240, *300249, *176947, *176894, *605081, *605035, *602044, *182860, *107271, *305100, *153390, *113730, *602689, *180069, *603518, *300017, *191275, *177061, *601693, *601789, *604241, *600934, *138160, *604424, *603868, *600174, *600718, *600523, *604141, *601009, *605251, *600481, *600874, *155550, *605227, *601017, *162230, 601138, *604157, *601212, *600763, *604110, *604158, *601107, *601326, 600621, *600587, 601137, *600917, *600855, *605058, *194355, *605194, *603291, *102720, *136425, *170715, *603216, *605547, *135630, *602926, *600168, *605002, *602474, *600157, *603025, *603893, *231200, *120090, *601966, *131230, *604722, *604721, *604515, *246700, *602101, *605628, *303630, *605787, *602857, *602285, *605708, *602488, *605025, *603817, *300051, *603293, *176878, *603646, 605707, 185860, *112205, *300187, *602654, *120070, *603648, *604850, *602655, *602514, *300118, *182309, *179590, *602701, *600759, *204200, *604170, *175100, #103580, *147670, *306400, *143100, *182870, *257220, *180380, #116920, *301000, *193300, *157147, *131550, *139200, *139130, *190195, *605406, *155760, *155960, *605734, *155970, *605385, *111700, *155975, *150370, 605709, *151430, *605438, *151510, *116952, *157655, *158105, *605777, *176877, *153619, *120131, *185430, *109190, *120190, *109170, *605093, *605250, *153432, *107777, *186590, *160993, *605699, *605698, *605813, *605697, *605616, *605300, *162060, *605219, *163970, *135620, *165040, *605478, *604964, *103195, *604932, *604923, *605906, *605496, *605914, *166490, 138277, *604915, *114070, *605213, *605933, *180297, *101000, *191163, *191164, *605101, *603167, *600772, *603164, *600708, *604001, *191328, *313440, *602672, *604009, *604299, *192974, *604256, *603048, *600515, *604221, *602632, *604196, *601179, 603290, *604661, *601023, *601110, *304800, *203200, *300212, *602933, *603352, *208900, *604418, *604838, *600551, #212140, *604837, *602049, *600552, *600553, *300213, *602574, *600583, *600932, *603452, *604775, *516020, *604617, *604464, *603498, *300145, *601523, *602694, *600632, *604762, *604492, *400015, *604504, *601717, *601728, *300242, *602426, *604194, *603821, *604730, *600695, *603823, *603869, *300241, *600707, *603822, *602370, *602202, *604193, *601181, *604089, *602507, *604195, *602306, *300284, *601805, *601895, *601275, *604660, *600752, *603820, *604192, *602207, *308230, *600894, *312600, *603199, *604029, *602500, *102680, *235200, #256300, *601633, #219700, 262890, *156225, *173470, *193400, *173910, *600354, *113705, *600065, *107741, *107400, *600024, *131195, *113811, #118220, *601638, *300011, *276903, *604144, *311770, *601758, #173900, *604592, *120120, *179605, *603130, *603372, *110750, *222900, *602509, *256100, *602469, *602281, *229300, *224100, *110900, *190180, *261600, *602997, *603616, *603189, 601791, *601567, *312700, *171060, *308700, *604027, *162643, *516000, *176261, *604028, *314850, #145980, *601383, *600930, *305900, *601253, *136350, *605537, *138140, *604033, *605070, *139250, *300500, *603967, *300041, *603866, #130600, *120150, *601050, *604942, *605204, *605248, *272750, *600163, *604235, *600682, *107266, *306900, *191092, #262500, *600106, *152790, *186720, *227650, *153700, *308380, *103390, *605646, *164920, *604478, #252650, *173850, *173350, *602505, *246530, *194380, *602575, *603030, #209920, *212138, #214100, *605767, *600582, *189980, #176200, *604653, *604678, *256550, *300037, *253700, #253300, #226700, *604766, #244400, *190000, *188040, *604824, *214500, #237500, *232300, *605014, *604477, *190930, *605124, *604475, *604594, #227810, *306700, #301050, *600135, *600143, *605145, #269920, *300104, *277900, *300135, *300231, *192500, *182138, *191190, *176805, *600185, *186591, *604889, *603051, *165360, *147545, *601040, #156575, *107269, *603009, *602934, *123825, *601081, *602924, *163890, *600381, *602909, *150330, *109690, *123900, *603434, *603491, *110700, *602581, *125647, #154700, *114760, *141900, *603690, *120220, *601199, #145500, *601309, *602382, *120325, *600877, *604205, *604090, *601497, *602377, *605464, *138720, *603728, *120950, *604026, *600580, *601610, *137167, *603960, *603931, *601880, *603126, *138190, *130130, *601997, *601975, *600395, *516040, *600418, *600650, *605245, *605172, *600509, *164761, *310400, *600308, *605109, *600544, *600359, *600103, *605267, *312610, *176100, *308100, *158070, *605123, *173325, #312750, *600839, *158120, #604369, *604465, *173510, #161200, *151525, *605369, *604237, *516050, #600886, *604517, *165180, *605381, *605399, *307800, *604365, *155740, *147795, 601709, *604673, *147730, *602122, *147557, *193245, *600978, *604990, *603261, *603274, *601007, *131100, *602941, *107941, *146710, *276901, *131244, *602872, *603411, *186357, *176290, *601066, *185050, *232200, *143030, *601843, #236700, *604122, *142800, *134638, *604985, *182380, *603930, *142410, *137060, *604586, *601193, *120650, *252500, *253800, *120930, *604858, *605874, 601274, *602158, *605873, *193210, *203100, *601295, *604095, #201710, *126150, *108740, #205400, *601373, *300167, *109545, *602894, *603361, #300257, *266200, *603401, *131390, *180470, *605908, *604798, #221770, *223360, *180901, *605641, *605745, *604018, *300200, *604603, *230800, *602676, #604004, *605692, *602640, *601599, *134637, *245900, *118425, 601614, *605725, *120110, *300189, *300035, *603102, *250800, *602282, *602458, *123610, *603754, *300278, *601463, *300224, *601581, *182160, *601653, *139191, *601733, *600748, *142460, *601194, *152390, *153620, *601615, *601814, *601617, *601613, *300191, #308300, *600798, 601858, *601872, *601597, #601588, *600821, *147840, *152427, *138850, *600823, *601492, *300256, *600840, *300267, *601411, *139080, *139090, 600851, *300334, *179080, *602095, *601284, *601282, *177200, *601681, *601252, *176000, *602184, *602188, *266510, #154020, *186711, *257200, *601711, *600667, *602241, *186745, *255125, *300126, *600644, *123890, *255120, #175200, *600004, *302060, *123580, *186760, *122561, *602316, *600017, *120940, 140300, *151690, *120700,

*602354, *600019, *600857, *182175, *600536, *158380, *600516, *120290, *600493, *182310, #252010, *182530, *186830, *601839, *142790, *159465, *118990, *250790, *248600, #248250, *186845, *601153, *142600, *116930, *114860, *171834, #303600, *186880, *600444, *142871, *601852, *602602, *602607, *114207, *186910, #232220, 600880, *134635, *112203, #112100, *111680, *231680, *311030, *111250, *111200, *134390, #226670, #145600, *226200, *602714, *171760, *133550, *602727, *161555, *602744, *602746, #131705, *602835, *600423, *176267, *602859, #600918, 277175, *602874, *601020, *109770, *600170, *217070, *173515, *602893, *147280, *154360, *171050, *108780, *176257, *600979, *600377, *108360, *204500, *170260, *146880, *154582, *601011, *600997, *602992, *201475, *603005, *190198, *147360, #270400, *600238, #164970, *306250, #126600, *193065, #181350, *106180, *602136, *600937, *603086, *603087, *307030, *182099, *103320, *601683, #192430, *103180, *102681, *192321, *600244, *191740, *191315, *603152, *102642, *191305, #266140, *100500, *600867, *604585, *604404, *604345, *603201, *605430, *603207, *603208, *605433, *604101, *603969, *605896, *604616, *605851, *605768, *604576, *605754, *605730, *605477, *603263, *605538, *603283, *604402, *605453, *605427, *603302, *605458, 603313, *604415, *603345, *605541, *603353, *605295, *603879, *605268, *605266, *605246, *603377, *603380, *605181, *604203, *603425, *603867, *605106, *605017, *603842, *604936, *603510, *604857, *605932, *605816, *603765, *603551, *605357, *605237, *604204, *603594, *605110, *604190, *603861, *604962, *603639, *603644, *605007, *605349, *604943, *604918, *604907, *603667, *603681, *605396, *605561, *603712, *603713, *605688, *605942, *604878, *604843, *604659, *604671, *603798, *604682, *604056, *604705, *603749, 602586, *603647, *602515, #602475, *603717, *602359, *602372, *602380, *602518, *603652, *602573, *603626, 602587, *603598, *602871, *603613, *603750, *603875, *602608, *602666, *602345, *602935, *603564, *603548, *603927, 601876, *602343, *603943, *603787, *601730, *601611, *602679, *603788, *602243, 603790, *601535, *603796, *601488, *601485, *602314, *601478, *604047, *604048, *602297, *604057, *602715, *602192, *601459, *601416, *603833, *602190, *604102, *602106, *604111, *602724, *603499, *602736, *601123, *601002, *600923, *601987, *604149, *601929, *600910, *600900, *600864, *604165, *600782, *602836, *600769, *600742, *602783, *601905, *600535, *604198, *601901, *600534, *602876, *603356, *600530, *604216, *604217, *602890, *602905, *600465, *600464, *600446, *602891, *603366, *601894, *604272, *603926, *603312, *600368, *602914, *600327, *603151, *603202, 602911, *602974, *603006, *601883, *603008, *600074, *603007, *603046, #603903, *604433, *600016, *603925, *516005, *516004, *516003, *601756, *604487, *516001, *313475, *313470, #307810, *604527, *604528, *601745, *604551, *604555, *603243, *603242, *603061, *603063, *603217, *300335, *300283, *300281, *604600, *300197, *603097, *603220, *601625, *604623, *603118, *601590, *604646, *300008, *601568, *300007, *275630, *601533, #275200, *270200, #261550, *604031, *604683, #254800, *251100, #242300, *604058, *604720, *240500, *233690, *232240, #226730, *223100, *222100, #220100, *216950, *604832, 212750, 212067, *604066, *193067, 601315, *193001, *604862, *604870, *191306, *600385, *604879, *191191, *601296, *604914, *190181, *604119, #188550, *604925, *188410, *601287, *604939, *188380, *604126, *604945, *604148, *188060, *604982, *186854, *604988, *186360, *186355, *185250, *600916, *605008, *605009, 185020, *600734, *605024, *182331, *605032, *605033, *182305, *180903, #179800, *179610, *605060, *179410, *178990, *176802, *605080, *176266, *176263, *176260, *600732, *173490, *604199, *173445, *173391, 172290, *605147, *605149, *171890, *600528, *171833, *605185, #170500, *605193, #168000, *605196, *167055, *605205, *605208, 166900, *605216, *162651, *162010, *600504, #161400, *604253, *160800, *159460, *154540, *605254, *605261, *153634, *600429, *153337, *600424, *605292, #604286, #152700, 152423, *152310, *151625, *600153, *604313, *151523, *150325, *150320, *150292, *603150, *150290, *150210, *605410, *605415, *605416, *605417, *605421, *603149, *604349, *147940, *600282, *147880, *146928, *146661, *600150, *146630, *142622, *600018, *605461, *138981, *138590, *600023, *138330, *605495, *138297, *605512, *138230, #136900, #301310, *516006, *605545, *605546, *136131, *134660, *134350, *516002, *605589, *131235, #130050, *605625, *126455, *126064, #125310, *605670, *604534, *125240, *123836, *123830, *123620, *605702, #122200, *120980, *120360, *118510, *114835, *605710, *605716, *605722, *114217, *604561, *113810, *111740, #110800, *605748, *605752, *604564, *110600, *603160, *109610, *605784, *107480, *107273, *603192, *300169, *106195, *105210, *104615, *104614, *104210, *103850, 103581, *605876, *605877, *605879, *103220, *605887, *300150, *102910, *102670, *102576, *605916, *604629, *102575, *102573, *300132, *101800, *605947

3) Channel (Member of Membrane Protein)

361 entries found, searching for "channel"

*176266, *600724, *182390, *123825, *114208, *114206, *176267, *114205, *601784, *600937, *114204, *603415, *600053, *114207, *114209, *605427, *604527, *604528, *600760, *601011, *192500, *118425, *600228, *176261, *602235, *600761, *600359, *300008, *182389, *600877, *602232, *176263, *182391, *601328, *600054, *603939, *602208, *601534, *600504, *602323, *603208, *601958, *603537, *601012, *601327, *600734, *602780, *602781, *604433, *603220, *182392, *605874, *605873, *601745, *603888, *603219, *602604, *603796, *302910, *602866, *601013, *602905, *602906, *603967, *600163, #170500, *152427, *180901, *176260, #601462, *603951, *601141, *604492, *600702, *602023, *600308, *602754, *107776, *176257, *602024, *601949, *605222, *601142, *602983, *193245, *600681, *176265, *600235, *176262, *176258, *605206, *604427, *605411, *603305, *601219, *600150, *604065, *602343, *605223, *605720, *603906, *138249, *138253, *600843, *604385, *600003, *600935, *603940, *602727, *602158, 602911, *600397, *602726, *600845, *605080, *600580, *602872, *602106, *176264, *603953, *605722, *300110, *138252, *604111, *602717, *602420, *600570, 600844, *603493, *600932, *605716, *138254, *603652, *300138, *605410, *176268, *605214, *605696, *300334, *604660, *176256, *605879, *603749, *603583, *602345, *604661, *603787, 603313, *602982, *604337, *600846, *604662, *300328, *300281, *602566, *602836, *604003, *603788, *603651, *602421, *107777, #177200, *100725, #219700, *100690, *100710, *160800, #603830, #183086, *600509, #220400, *601144, *173910, *180902, *605692, *264350, *160900, *145600, #255700, *602076, *603061, *601313, *154275, *604233, *604532, *108500, #121201, *170400, *300225, *121014, *139311, #125800, *160120, *118503, 601439, *141500, *168300, *304040, #601887, #256450, *186945, *154276, *300009, *216900, #600040, *601014, *601042, *602512, *601383, *605445, *602368, *603831, #117000, *601218, *108745, *605248,

177735, #173900, *601212, *182139, *601059, *600039, *601485, *180903, *186360, *603319, #600101, *118509, *600109, #121200, *600170, *604187, *176975, *137163, #310468, #263800, #262300, *603750, *600229, *124030, *602251, #603829, *137143, #145500, *600669, *147450, *154050, *603353, *600516, *601157, *600855, *601154, *602522, *249210, *600968, #252650, *171060, *600919, *156490, #259700, #601678, *601764, #310500, *131244, *300041, *121011, *125950, *114180, *602974, *600637, *113730, *118504, *605145, *604669, *118800, *121013, *121015, *138491, *600421, *104610, *604045, *604594, *131230, *605487, *138247, *600467, *602485, *602481, *138251, *137192, *602403, 600851, *277900, *603785, *603152, *603199, *603475, #168600, #272120, *170280, *603852, #241200, *603053, *600465, *603034, *142461, *164920, *137164, *600884, *600442, *123885, *604001, *600232, *232200, *171050, *602103, *602014, *300211, *600983, *602887, *604415, *604418, *300242, #300071, *604471, *600837, 168350, *118511, 193007, *600300, *604654, #601820, *180297, *600046, *603853, *604678, *604693, #604772, *118508, *603855, *605204, #254210, *182099, *182307, #130600, *601109, *114080, *300103, *182860, *605438, *601129, *603964, *600019, *516060, #185000, *138079, *104210, *605818, *603418, *305990, *305450

4) Extracellular Matrix 218 entries found, searching for "extracellular matrix"

*605912, *603479, *602201, *604633, *601418, *601548, *115437, *154870, *600754, *602261, *602285, *602262, *134797, *120361, *604629, *604871, *603321, *603320, *601807, #154700, *116935, *185261, *120360, *185250, *605470, *603767, *253700, *190180, *128239, *308700, *276901, *193300, *120324, *188826, *602109, *155760, *600514, *600261, #177170, *600536, *147557, #116920, *150240, *601313, *120140, 601614, *605158, *120150, *120180, #200610, *605127, *193400, *192240, #173900, *152200, #136900, *135821, #130070, *120320, *120220, *112260, *310200, *600900, *600262, *605670, *600985, *179590, #245150, *602574, *601463, 183850, *601211, *604241, *600758, *186745, *604710, *602369, *602090, *190182, *192975, *602178, *230740, *600065, *601652, *158106, *190181, *156790, #158810, *193210, *155120, *192977, *193065, #226700, *187380, *231050, *182120, *188060, *186355, 163200, *164010, #156550, *151510, *150370, *253800, *156225, *150325, #194050, *150290, *216550, *147620, *600215, *222600, *147559, *165380, *182888, *600491, *146650, *146640, *600564, *600596, *600616, *600700, *600742, *138297, *182889, *154705, *600930, *301870, *153619, *601050, *601090, *601105, *165070, *305370, *135820, *130660, *310300, *601492, *128240, *601587, #126600, *601636, *600119, *601692, *601728, *125485, 601858, *601915, *602048, *175100, *602108, *121010, *600245, *120470, *120328, *120325, *602264, *120280, *602366, *600309, *602402, *602415, *602428, *602453, *602505, #166210, *602600, *602941, *603005, *603196, 603209, *603221, *603234, *603319, *120250, *120210, *120120, *603489, *603551, *118938, *603799, *603842, *603924, *603963, *604042, *604063, *604149, *604160, *601028, *604467, *604510, *604592, *116930, *116806, *601284, *604724, *604806, *604807, *604808, *107269, *605007, *605008, *605009, *600214, *600076, *605174, *605175, *605292, *605343, *605351, #600204, *605497, *605546, *605587, *605623, *600211, *605702, *103320

In addition to these, the various keywords shown in the above-mentioned categorization or others can be used for the OMIM search and the result may suggest the involvement thereof in diseases.

Further, the use of nucleotide sequences of cDNAs of the present invention enables analyzing the expression frequency of genes corresponding to the cDNAs. In addition, functions of the genes can be predicted based on the information obtained by the expression frequency analysis.

There are several methods for analyzing the expression levels of genes involved in diseases. Differences in gene expression levels between diseased and normal tissues are studied by the analytical methods using, for example, Northern hybridization, RT-PCR, DNA microarray, etc. (Experimental Medicine, Vol. 17, No. 8, 980-1056 (1999); Cell Engineering (additional volume) DNA Microarray and Advanced PCR Methods, Muramatsu & Nawa (eds.), Shujunsya (2000)). By computer analysis, in addition to these analysis methods, the nucleotide sequences of expressed genes can be compared to analyze the expression frequency. For example, there is a database called "BODYMAP"; gene clones are extracted at random from cDNA libraries of various tissues and/or cells, and the clones homologous to one another are assigned to a single cluster based on the information of nucleotide sequence homology at the 3'-end; genes are classified into any clusters, and the numbers of clones in the respective clusters are compared to gain the information on expression frequency (available on the world wide web at bodymap.ims.u-tokyo.ac.jp/).

When explicit difference in the expression levels between diseased tissues and normal tissues is observed for a gene by these analytical methods, it can be conclude that the gene is closely involved in a disease or disorder. Instead of diseased tissues, when gene expression is explicitly different between normal cells and cells reproducing disease-associated specific features, it can be concluded that the gene is closely involved in a disease or disorder.

From the 2443 clones whose full-length nucleotide sequences had been revealed, genes involved in particular pathology or functions were selected by the use of databases shown below (see Example 7; "Expression frequency analysis in silico"). The database used in the analyses of the present invention contains nucleotide sequences of 1,402,070 clones, and the population of the database is large enough for the analysis. The sequence information in the database was obtained by selecting cDNA clones at random from cDNA libraries derived from the various tissues and cells shown in Example 1 and determining the 5'-end sequences thereof.

Then, the nucleotide sequences of respective clones in this database were categorized (clustered) based on the nucleotide sequence homology determined with a search program; the number of clones belonging to every cluster of each library was determined and normalized; thus, the ratio of a certain gene in a cDNA library was determined. This analysis provided the information of the expression frequency of a gene in a tissue or cell that is the source of the cDNA library.

Then, in order to analyze the expression of genes corresponding to the nucleotide sequences of cDNAs of the present invention in tissues and cells, the libraries from the tissues or cells, which had been used in the large-scale cDNA analyses, were taken as subjects to compare the expression levels between different tissues or cells. Namely, the expression frequency was analyzed by comparing the previously normalized values between tissues or cells from which 600 or more cDNA clones whose nucleotide sequences had been analyzed were derived. The result of this analysis showed that the cDNA clones corresponded to the genes involved in the pathology and functions, which are indicated below. Each value in Tables 3 to 51 indicated below represents a relative expression frequency; the higher the value, the higher the expression level.

Osteoporosis-related Genes

Osteoporosis is a pathology in which bones are easily broken owing to overall decrease in components of bone. The onset correlates to the balance between the functions of osteoblast producing bone and osteoclast absorbing bone, namely bone metabolism. Thus, the genes involved in the increase of osteoclasts differentiating from precursor cells of monocyte/macrophage line (Molecular Medicine 38. 642-648. (2001)) are genes involved in osteoporosis relevant to bone metabolism.

A nucleotide sequence information-based analysis was carried out to identify the genes whose expression frequencies are higher or lower in CD34+ cell (cell expressing a glycoprotein CD34) treated with the osteoclast differentiation factor (Molecular Medicine 38. 642-648. (2001)) than in the untreated CD34+ cell, which is the precursor cell of monocyte/macrophage line. The result of comparative analysis for the frequency between the cDNA libraries prepared from the RNA of CD34+ cells (CD34C) and from the RNA of CD34+ cells treated with the osteoclast differentiation factor (D30ST, D60ST or D90ST) showed that the HEART20049410 expression levels were not detected as being different between the two conditions.

Genes Involved in Neural Cell Differentiation

Genes involved in neural cell differentiation are useful for treating neurological diseases. Genes with varying expression levels in response to induction of cellular differentiation in neural cells are thought to be involved in neurological diseases.

A survey was performed for genes whose expression levels are varied in response to induction of differentiation (stimulation by retinoic acid (RA) or growth inhibitor treatment after RA stimulation) in cultured cells of a neural strain, NT2. The result of comparative analysis of cDNA libraries derived from undifferentiated NT2 cells (NT2RM) and the cells subjected to the differentiation treatment (NT2RP, NT2R1 or NT2NE) showed that the HEART20049410 expression levels were not detected as being different between the two conditions.

Cancer-related Genes

It has been assumed that, distinct from normal tissues, cancer tissues express a distinct set of genes, and thus the expression thereof can contribute to the carcinogenesis in tissues and cells. Thus, genes whose expression patterns in cancer tissues are different from those in normal tissues are cancer-related genes. Search was carried out for the genes whose expression levels in cancer tissues were different from those in normal tissues.

The result of comparative analysis of cDNA libraries derived from breast tumor (TBAES) and normal breast (BEAST) showed that the genes whose expression levels were different between the two were 35 clones.

The result of comparative analysis of cDNA libraries derived cervical tumor (TCERX) and normal cervical duct (CERVX) showed that the genes whose expression levels were different between the two were 11 clones.

The result of comparative analysis of cDNA libraries derived from colon tumor (TCOLN) and normal colon (COLON) showed that the genes whose expression levels were different between the two were 25 clones.

The result of comparative analysis of cDNA libraries derived from esophageal tumor (TESOP) and normal esophagus (NESOP) showed that the genes whose expression levels were different between the two were 41 clones.

The result of comparative analysis of cDNA libraries derived from kidney tumor (TKIDN) and normal kidney (KIDNE) showed that the genes whose expression levels were different between the two were 175 clones.

The result of comparative analysis of cDNA libraries derived from liver tumor (TLIVE) and normal liver (LIVER) showed that the genes whose expression levels were different between the two were 47 clones.

The result of comparative analysis of cDNA libraries derived from lung tumor (TLUNG) and normal lung (HLUNG) showed that the genes whose expression levels were different between the two were 62 clones.

The result of comparative analysis of cDNA libraries derived from ovary tumor (TOVER) and normal ovary (NOVER) showed the genes whose expression levels were different between the two were 23 clones.

The result of comparative analysis of cDNA libraries derived from stomach tumor (TSTOM) and normal stomach (STOMA) showed that the genes whose expression levels were different between the two were 70 clones.

The result of comparative analysis of cDNA libraries derived from uterine tumor (TUTER) and normal uterus (UTERU) showed that the genes whose expression levels were different between the two were 236 clones.

The result of comparative analysis of cDNA libraries derived from tongue cancer (CTONG) and normal tongue (NTONG) showed that the genes whose expression levels were different between the two were 232 clones.

Further, there is a method to search for genes involved in development and differentiation, which is the expression frequency analysis in which the expression levels of genes are compared between developing and/or differentiating tissues and/or cells and adult tissues and/or cells. The genes involved in tissue development and/or differentiation are genes participating in tissue construction and expression of function, and thus are useful genes, which are available for regenerative medicine aiming at convenient regeneration of injured tissues.

By using the information of gene expression frequency gained from the database of 5'-end nucleotide sequences described above, genes involved in development or differentiation of particular tissues were selected from the 2443 clones whose full-length nucleotide sequence had been revealed (see Example 7).

The result of comparative analysis of cDNA libraries derived from fetal brain (FCBBF, FEBRA or OCBBF) and adult brain (BRACE, BRALZ, BRAMY, BRAWH, BRCAN, BRCOC, BRHIP, BRSSN, BRSTN or BRTHA) showed that the genes whose expression levels were different between the two were 1195 clones.

The result of comparative analysis of cDNA libraries derived from fetal heart (FEHRT) and adult heart (HEART) showed that the genes whose expression levels were different between the two were 45 clones indicated in Table 3. HEART20049410 is not detected in fetal heart tissue, but is expressed adult heart tissue.

The result of comparative analysis of cDNA libraries derived from fetal kidney (FEKID) and adult kidney (KIDNE) showed that the genes whose expression levels were different between the two were 118 clones.

The result of comparative analysis of cDNA libraries derived from fetal lung (FELNG) and adult lung (HLUNG) showed that the genes whose expression levels were different between the two were 63 clones. These genes are involved in regeneration of tissues and/or cells.

The expression frequency or the like can be analyzed by PCR based on the nucleotide sequences of cDNAs of the present invention. There are some known methods for comparing the quantities of amplification products obtained by PCR. For example, the band intensities can be determined by ethidium bromide staining. With R1-labeled or fluorescently labeled primers, the R1 signal or fluorescence intensity can be assayed for the quantity of labeled amplification products. Alternatively, the quantity of amplification products can also be determined by measuring the R1 signal or the fluorescence intensity from the R1-labeled or fluorescently labeled probe hybridizing to the products. The assay results thus obtained are compared and then the clones exhibiting differences in the expression levels can be selected.

There are some quantitative PCR methods: a PCR method using internal standards; a competitive PCR, in which the quantification is achieved by adding, to a sample, a dilution series of a known quantity of a template RNA and by comparing the quantity of an amplification product derived from the RNA of interest with the quantity of an amplification product derived from the template RNA. These methods overcome the problems of errors in the amount of amplification products among tubes and of the plateau effect. ATAC-PCR (Adaptor-tagged competitive PCR) is a method of competitive PCR which is practiced by using multiple adapters of different sizes attached to a gene whose 3'-end nucleotide sequence has previously been determined. The ratio of expression frequency of a single mRNA species from a number of tissues (cells) can be assayed in a single step (Nucleic Acids Research 1997, 25(22): 4694-4696; "DNA Micro-array and Advanced PCR Techniques", Cell Technology, supplement, Eds., Muramatsu and Nawa (Shujunsha, 2000): 104-112).

If it is observed, by using these analytical methods, that the expression levels of genes are evidently varied during major cellular events (such as differentiation and apoptosis), the genes are involved in the cellular events and accordingly are candidates for disease- and/or disorder-related genes. Further, genes exhibiting tissue-specific expression are genes playing important parts in the tissue functions and, therefore, can be candidates for genes involved in diseases and/or disorders affecting the tissues.

For example, inflammation is an important biological response that is known to be involved in various diseases. The representative inflammation-inducing factors include TNF-α (Tumor Necrosis Factor-alpha). There exists a signaling cascade activated by TNF-α stimulations, wherein NF-κB is a transducing molecule (Cell 1995, 80:529-532). It has also been revealed that many inflammation-related genes, including IL-2, IL-6 and G-CSF, are varied in the expression levels thereof in response to the signal through the pathway (Trends Genet. 1999, 15(6): 229-235). It is assumed that genes whose expression levels are varied in response to the stimulation of TNF-α also participate in inflammation.

Further, the infection of *Helicobacter pylori* to the gastric epithelia is known to cause gastritis and gastroduodenal ulcer (Mebio 2000, July, 17(7): 16-33). Thus, the genes whose expression levels are altered depending on co-culturing cells with *Helicobacter pylori* may be involved in gastritis and gastroduodenal ulcer. A recent study has suggested that *Helicobacter pylori* strongly activates the NF-κB pathway (Gastroenterology 2000, 119: 97-108).

THP-1 cell, which is a human monocyte cell line, was cultured in the presence of TNF-α (Tumor Necrosis Factor-alpha). The genes whose expression levels were altered owing to the presence of TNF-α were searched for, and the result showed that the clones whose expression levels were increased or decreased owing to the presence of TNF-α did not include HEART20049410.

MKN45, which is a gastric cancer cell line, was co-cultured with *Helicobacter pylori*. The genes whose expression levels were altered owing to the presence of *Helicobacter pylori* were searched for, and the result showed that the clones whose expression levels were increased or decreased owing to the presence of *Helicobacter pylori* did not include HEART20049410.

For example, if the polypeptide encoded by the cDNA of the present invention is a regulatory factor of cellular conditions such as growth and differentiation, it can be used for developing medicines as follows. The polypeptide or antibody provided by the invention is injected into a certain kind of cells by microinjection. Then, using the cells, it is possible to screen low molecular weight compounds, etc. by measuring the change in the cellular conditions, or the activation or inhibition of a particular gene. The screening can be performed as follows.

First, the polypeptide is expressed and purified as recombinant. The purified polypeptide is microinjected into cells such as various cell lines, or primary culture cells, and the cellular change such as growth and differentiation can be examined. Alternatively, the induction of genes whose expression is known to be involved in a particular change of cellular conditions may be detected by the amount of mRNA or polypeptide. Alternatively, the amount of intracellular molecules (low molecular weight compounds, etc.) that is changed by the function of the gene product (polypeptide) which is known to be involved in a particular change of cellular conditions may be detected.

The compounds to be screened (both low and high molecular compounds are acceptable) can be added to the culture media and assessed for their activity by measuring the change of the cellular conditions.

Instead of microinjection, cell lines introduced with the gene obtained in the invention can be used for the screening. If the gene product is turn out to be involved in a particular change in the cellular conditions, the change of the product can be used as a measurement for screening. Once a compound is screened out which can activate or inhibit the function of the polypeptide of the invention, it can be applied for developing medicines.

If the polypeptide encoded by the cDNA of the present invention is a secretory protein, membrane protein, or protein involved in signal transduction, glycoprotein, transcription, or diseases, it can be used in functional assays for developing medicines.

In case of a membrane protein, it is most likely to be a polypeptide that functions as a receptor or ligand on the cell surface. Therefore, it is possible to reveal a new relationship between a ligand and receptor by screening the membrane protein of the invention based on the binding activity with the known ligand or receptor. Screening can be performed according to the known methods.

For example, a ligand against the polypeptide of the invention can be screened in the following manner. Namely, a ligand that binds to a specific polypeptide can be screened by a method comprising the steps of: (a) contacting a test sample with the polypeptide of the invention or a partial peptide thereof, or cells expressing these, and (b) selecting a test sample that binds to said polypeptide, said partial peptide, or said cells.

On the other hand, for example, screening using cells expressing the polypeptide of the present invention that is a receptor protein can also be performed as follows. It is possible to screen receptors that is capable of binding to a specific polypeptide by using procedures (a) attaching the sample cells to the polypeptide of the invention or its partial peptide, and (b) selecting cells that can bind to the said polypeptide or its partial peptide.

In a following screening as an example, first the polypeptide of the invention is expressed, and the recombinant polypeptide is purified. Next, the purified polypeptide is labeled, binding assay is performed using a various cell lines or primary cultured cells, and cells that are expressing a receptor are selected (Growth and differentiation factors and their receptors, Shin-Seikagaku Jikken Kouza Vol. 7 (1991) Honjyo, Arai, Taniguchi, and Muramatsu edit, p203-236, Tokyo-Kagaku-Doujin). A polypeptide of the invention can be labeled with RI such as $^{125}I$, and enzyme (alkaline phosphatase etc.).

Alternatively, a polypeptide of the invention may be used without labeling and then detected by using a labeled antibody against the polypeptide. The cells that are selected by the above screening methods, which express a receptor of the polypeptide of the invention, can be used for the further screening of an agonists or antagonists of the said receptor.

Once the ligand binding to the polypeptide of the invention, the receptor of the polypeptide of the invention or the cells expressing the receptor are obtained by screening, it is possible to screen a compound that binds to the ligand and receptor. Also it is possible to screen a compound that can inhibit both bindings (agonists or antagonists of the receptor, for example) by utilizing the binding activities.

When the polypeptide of the invention is a receptor, the screening method comprises the steps of (a) contacting the polypeptide of the invention or cells expressing the polypeptide of the invention with the ligand, in the presence of a test sample, (b) detecting the binding activity between said polypeptide or cells expressing said polypeptide and the ligand, and (c) selecting a compound that reduces said binding activity when compared to the activity in the absence of the test sample. Furthermore, when the polypeptide of the invention is a ligand, the screening method comprises the steps of (a) contacting the polypeptide of the invention with its receptor or cells expressing the receptor in the presence of samples, (b) detecting the binding activity between the polypeptide and its receptor or the cells expressing the receptor, and (c) selecting a compound that can potentially reduce the binding activity compared to the activity in the absence of the sample.

Samples to screen include cell extracts, expressed products from a gene library, synthesized low molecular compound, synthesized peptide, and natural compounds, for example, but are not construed to be listed here. A compound that is isolated by the above screening using a binding activity of the polypeptide of the invention can also be used as a sample.

A compound isolated by the screening may be a candidate to be an agonist or an antagonist of the receptor of the polypeptide. By utilizing an assay that monitors a change in the intracellular signaling such as phosphorylation which results from reduction of the binding between the polypeptide and its receptor, it is possible to identify whether the obtained compound is an agonist or antagonist of the receptor. Also, the compound may be a candidate of a molecule that can inhibit the interaction between the polypeptide and its associated proteins (including a receptor) in vivo. Such compounds can be used for developing drugs for precaution or cures of a disease in which the polypeptide is involved.

Secretory proteins may regulate cellular conditions such as growth and differentiation. It is possible to find out a novel factor that regulates cellular conditions by adding the secretory protein of the invention to a certain kind of cell, and performing a screening by utilizing the cellular changes in growth or differentiation, or activation of a particular gene.

The screening can be performed, for example, as follows. First, the polypeptide of the invention is expressed and purified in a recombinant form. Then, the purified polypeptide is added to a various kind of cell lines or primary cultured cells, and the change in the cell growth and differentiation is monitored. The induction of a particular gene that is known to be involved in a certain cellular change is detected by the amounts of mRNA and polypeptide. Alternatively, the amount of an intracellular molecule (low-molecular-weight compounds, etc.) that is changed by the function of a gene product (polypeptide) that is known to function in a certain cellular change is used for the detection.

Once the screening reveals that the polypeptide of the invention can regulate cellular conditions or the functions, it is possible to apply the polypeptide as a pharmaceutical and diagnostic medicine for related diseases by itself or by altering a part of it into an appropriate composition.

As is above described for membrane proteins, the secretory protein provided by the invention may be used to explore a novel ligand-receptor interaction using a screening based on the binding activity to a known ligand or receptor. A similar method can be used to identify an agonist or antagonist. The resulting compounds obtained by the methods can be a candidate of a compound that can inhibit the interaction between the polypeptide of the invention and an interacting molecule (including a receptor). The compounds may be able to use as a preventive, therapeutic, and diagnostic medicine for the diseases, in which the polypeptide may play a certain role.

Proteins involved in signal transduction or transcription may be a factor that affects a certain polypeptide or gene in response to intracellular/extracellular stimuli. It is possible to find out a novel factor that can affect a polypeptide or gene by expressing the polypeptide provided by the invention in a certain types of cells, and performing a screening utilizing the activation of a certain intracellular polypeptide or gene.

The screening may be performed as follows. First, a transformed cell line expressing the polypeptide is obtained. Then, the transformed cell line and the untransformed original cell line are compared for the changes in the expression of a certain gene by detecting the amount of its mRNA or polypeptide. Alternatively, the amount of an intracellular molecule (low molecular weight compounds, etc.) that is changed by the function of a certain gene product (polypeptide) may be used for the detection. Furthermore, the change of the expression of a certain gene can be detected by introducing a fusion gene that comprises a regulatory region of the gene and a marker gene (luciferase, β-galactosidase, etc.) into a cell, expressing the polypeptide provided by the invention into the cell, and estimating the activity of a marker gene product (polypeptide).

If the polypeptide or gene of the invention is involved in diseases, it is possible to screen a gene or compound that can regulate its expression and/or activity either directly or indirectly by utilizing the polypeptide of the present invention.

For example, the polypeptide of the invention is expressed and purified as a recombinant polypeptide. Then, the polypeptide or gene that interacts with the polypeptide of the invention is purified, and screened based on the binding. Alternatively, the screening can be performed by adding with a compound of a candidate of the inhibitor added in advance and monitoring the change of binding activity. In another method, a transcription regulatory region locating in the 5'-upstream of the gene encoding the polypeptide of the invention that is capable of regulating the expression of other genes is obtained, and fused with a marker gene. The fusion is introduced into a cell, and the cell is added with compounds to explore a regulatory factor of the expression of the said gene.

The compound obtained by the screening can be used for developing pharmaceutical and diagnostic medicines for the diseases in which the polypeptide of the present invention is involved. Similarly, if the regulatory factor obtained in the screening is turn out to be a polypeptide, compounds that can newly affect the expression or activity of the polypeptide may be used as a medicine for the diseases in which the polypeptide of the invention is involved.

If the polypeptide of the invention has an enzymatic activity, regardless as to whether it is a secretory protein, membrane protein, or proteins involved in signal transduction, glycoprotein, transcription, or diseases, a screening may be performed by adding a compound to the polypeptide of the invention and monitoring the change of the compound. The enzymatic activity may also be utilized to screen a compound that can inhibit the activity of the polypeptide.

In a screening given as an example, the polypeptide of the invention is expressed and the recombinant polypeptide is purified. Then, compounds are contacted with the purified polypeptide, and the amount of the compound and the reaction products is examined. Alternatively, compounds that are candidates of an inhibitor are pretreated, then a compound (substrate) that can react with the purified polypeptide is added, and the amount of the substrate and the reaction products is examined.

The compounds obtained in the screening may be used as a medicine for diseases in which the polypeptide of the invention is involved. Also they can be applied for tests that examine whether the polypeptide of the invention functions normally in vivo.

Whether the secretory protein, membrane protein, signal transduction-related protein, glycoprotein-related protein, or transcription-related protein of the present invention is a novel protein involved in diseases or not is determined in another method than described above, by obtaining a specific antibody against the polypeptide of the invention, and examining the relationship between the expression or activity of the polypeptide and a certain disease. In an alternative way, it may be analyzed referred to the methods in "Molecular Diagnosis of Genetic Diseases" (Elles R. edit, (1996) in the series of "Method in Molecular Biology" (Humana Press).

Proteins involved in diseases are targets of screening as mentioned, and thus are very useful in developing drugs which regulate their expression and activity. Also, the proteins are useful in the medicinal industry as a diagnostic marker of the related disease or a target of gene therapy.

Compounds isolated as mentioned above can be administered patients as it is, or after formulated into a pharmaceutical composition according to the known methods. For example, a pharmaceutically acceptable carrier or vehicle, specifically sterilized water, saline, plant oil, emulsifier, or suspending agent can be mixed with the compounds appropriately. The pharmaceutical compositions can be administered to patients by a method known to those skilled in the art, such as intraarterial, intravenous, or subcutaneous injections. The dosage may vary depending on the weight or age of a patient, or the method of administration, but those skilled in the art can choose an appropriate dosage properly. If the compound is encoded by polynucleotide, the polynucleotide can be cloned into a vector for gene therapy, and used for gene therapy. The dosage of the polynucleotide and the method of its administration may vary depending on the weight or age of a patient, or the symptoms, but those skilled in the art can choose properly.

The present invention further relates to databases comprising at least a sequence of polynucleotide and/or polypeptide, or a medium recorded in such databases, selected from the sequence data of the nucleotide and/or the amino acids indicated in Table 1. The term "database" means a set of accumulated information as machine-searchable and readable information of nucleotide sequence. The databases of the present invention comprise at least one of the novel nucleotide sequences of polynucleotides provided by the present invention. The databases of the present invention can consist of only the sequence data of the novel polynucleotides provided by the present invention or can comprise other information on nucleotide sequences of known full-length cDNAs or ESTs. The databases of the present invention can be comprised of not only the information on the nucleotide sequences but also the information on the gene functions revealed by the present invention. Additional information such as names of DNA clones carrying the full-length cDNAs can be recorded or linked together with the sequence data in the databases.

The database of the present invention is useful for gaining complete gene sequence information from partial sequence information of a gene of interest. The database of the present invention comprises nucleotide sequence information of full-length cDNAs. Consequently, by comparing the information in this database with the nucleotide sequence of a partial gene fragment yielded by differential display method or subtraction method, the information on the full-length nucleotide sequence of interest can be gained from the sequence of the partial fragment as a starting clue.

The sequence information of the full-length cDNAs constituting the database of the present invention contains not only the information on the complete sequences but also extra information on expression frequency of the genes as well as homology of the genes to known genes and known polypeptides. Thus the extra information facilitates rapid functional analyses of partial gene fragments. Further, the information on human genes is accumulated in the database of the present invention, and therefore, the database is useful for isolating a human homologue of a gene originating from other species. The human homologue can be isolated based on the nucleotide sequence of the gene from the original species.

At present, information on a wide variety of gene fragments can be obtained by differential display method and subtraction method. In general, these gene fragments are utilized as tools for isolating the full-length sequences thereof. When the gene fragment corresponds to an already-known gene, the full-length sequence is easily obtained by comparing the partial sequence with the information in known databases. However, when there exists no information corresponding to the partial sequence of interest in the known databases, cDNA cloning should be carried out for the full-length cDNA. It is often difficult to obtain the full-length nucleotide sequence using the partial sequence information as an initial clue. If the full-length of the gene is not available, the amino acid sequence of the polypeptide encoded by the gene remains unidentified. Thus the database of the present invention can contribute to the identification of full-length cDNAs corresponding to gene fragments, which cannot be revealed by using databases of known genes.

The present invention has provided 2443 polynucleotides. As has not yet proceeded the isolation of full-length cDNA within the human, the invention has great significance. It is known that secretory proteins, membrane proteins, signal transduction-related proteins, glycoprotein-related proteins, transcription-related proteins, and so on are involved in many diseases. The genes and proteins involved in diseases are useful for developing a diagnostic marker or medicines for regulation of their expression and activity, or as a target of gene therapy.

In particular, cDNA assumed to encode secretory proteins, which were provided by this invention, are very important for the industry since the encoded proteins themselves are expected to be useful as pharmaceutical agents and many disease-related genes may be included in them. In addition, membrane proteins, signal transduction-related proteins, transcription-related proteins, disease-related proteins, and genes encoding them can be used as indicators for diseases, etc. These cDNA are also very important for the industry, which are expected to regulate the activity or expression of the encoded protein to treat diseases, etc.

Any patents, patent applications, and publications cited herein are incorporated by reference.

The invention is illustrated more specifically with reference to the following examples, but is not to be construed as being limited thereto.

EXAMPLE 1

Preparation of cDNA Library by Oligo-Capping (1) Extraction and Purchase of mRNA Total RNAs as mRNA sources were extracted from human tissues (shown below) by the method as described in the reference (J. Sambrook, E. F. Fritsch & T. Maniatis, Molecular Cloning Second edition, Cold Spring harbor Laboratory Press, 1989). Further, by the method as described in the reference (J. Sambrook, E. F. Fritsch & T. Maniatis, Molecular Cloning Second edition, Cold Spring harbor Laboratory Press, 1989), total RNAs as mRNA sources were extracted from human culture cells and human primary culture cells (shown below) which had been cultivated by the methods described in the catalogs.

The library names and the origins are indicated below in the order of "Library name: Origin". When a library was prepared by the subtraction method, the item is followed by a description of how to prepare the subtracted library.

<Extraction of mRNA from Human Tissues>
NTONG: Normal tongue;
CTONG: Tongue cancer;
FCBBF: Fetal brain;
OCBBF: Fetal brain;
PLACE: Placenta;
SYNOV: Synovial membrane tissue (from rheumatoid arthritis);
CORDB: Cord blood.

<Extraction of mRNA from Culture Cells>
BNGH4: H4 cells (ATCC #HTB-148);
IMR32: IMR32 cells (ATCC #CCL-127);
SKNMC: SK-N-MC cells (ATCC #HTB-10);
3NB69: NB69 cells (RCB #RCB0480);
BGGI1: GI1 cells (RCB #RCB0763);
NB9N4: NB9 cells (RCB #RCB0477);
SKNSH: SK-N-SH cells (RCB #RCB0426);
AHMSC: Human mesenchymal (HMSC) cells;
CHONS: Chondrocytes;
ERLTF: TF-1 cells (erythroleukemia);
HELAC: HeLa cells;
JCMLC: Leukemia, myelogenous;
MESTC: Mesenchyme stem cells;
N1ESE: Mesenchymal stem cells;
NCRRM: Embryonal carcinoma;
NCRRP: Embryonal carcinoma treated with retinoic acid (RA) to induce the differentiation;
T1ESE: Mesenchymal stem cells treated with trichostatin and 5-azacytidine to induce the differentiation;
NT2RM: NT2 cells (STARATAGENE #204101);
NT2RP: NT2 cells treated with retinoic acid (RA) for 5 weeks to induce the differentiation;
NT2R1: NT2 cells treated with RA for 5 weeks to induce the differentiation, followed by the treatment with the growth inhibitor for 2 weeks;
NT2NE: NT2 cells were treated with RA and the growth inhibitor for the neuronal differentiation, and the resultant neurons were concentrated and harvested (NT2 Neuron);
NTISM: NT2 cells (STARATAGENE #204101) were treated with RA for 5 weeks to induce the differentiation, and then treated with the growth inhibitor for 2 weeks; mRNA was prepared from the cells and a cDNA library was constructed from the mRNA; the cDNAs of the library whose nucleotide sequences were shared by those of mRNAs from undifferentiated NT2 cells were subtracted by using a Subtract Kit (Invitrogen #K4320-01); the subtracted library (NT2RI-NT2RM) was provided by this procedure.

RCB indicates that the cell was provided by the Cell Bank, RIKEN GENE BANK, The Institute of Physical and Chemical Research; ATCC indicates that the cell was provided by American Type Culture Collection.

<Extraction of mRNA from Primary Culture Cells>
ASTRO: Normal human astrocyte NHA5732, Takara Shuzo #CC2565;
DFNES: Normal human dermal fibroblast (neonatal skin); NHDF-Neo NHDF2564, Takara Shuzo #CC2509;
MESAN: Normal human mesangial cell NHMC56046-2, Takara Shuzo #CC2559;
NHNPC: Normal human neural progenitor cell NHNP5958, Takara Shuzo #CC2599;
PEBLM: Normal human peripheral blood mononuclear cell HPBMC5939, Takara Shuzo #CC2702;
HSYRA: Human synoviocyte HS-RA (from rheumatoid arthritis), Toyobo #T404K-05;
PUAEN: Normal human pulmonary artery endothelial cells, Toyobo #T302K-05;
UMVEN: Normal human umbilical vein endothelial cell HUVEC, Toyobo #T200K-05;
HCASM: Normal human coronary artery smooth muscle cell HCASMC, Toyobo #T305K-05;
HCHON: Normal human chondrocyte HC, Toyobo #T402K-05;
HHDPC: Normal human dermal papilla cell HDPC, Toyobo #THPCK-001;
CD34C: CD34+ cells (AllCells, LLC #CB14435M);
D30ST: CD34+ cells treated with the osteoclast differentiation factor (ODF) for 3 days to induce the differentiation;
D60ST: CD34+ cells treated with ODF for 6 days to induce the differentiation;
D90ST: CD34+ cells treated with ODF for 9 days to induce the differentiation;
ACTVT: Activated T-cells;
LYMPB: Lymphoblasts, EB virus transferred B cells;
NETRP: Neutrophils.

Then, total RNAs extracted from the following human tissues were purchased and used as mRNA sources. The library names and the origins are indicated below in the order of "Library name: Origin". When a library was prepared by the subtraction method, the item is followed by a description of how to prepare the subtracted library.

<Purchase of Total RNA Containing mRNA Extracted from Human Tissues>
ADRGL: Adrenal gland, CLONTECH #64016-1;
BRACE: Brain (cerebellum), CLONTECH #64035-1;
BRAWH: Whole brain, CLONTECH #64020-1;
FEBRA: Fetal brain, CLONTECH #64019-1;
FELIV: Fetal liver, CLONTECH #64018-1;
HEART: Heart, CLONTECH #64025-1;
HLUNG: Lung, CLONTECH #64023-1;
KIDNE: Kidney, CLONTECH #64030-1;
LIVER: Liver, CLONTECH #64022-1;
MAMGL: Mammary Gland, CLONTECH #64037-1;
PANCR: Pancreas, CLONTECH #64031-1;
PROST: Prostate, CLONTECH #64038-1;
SALGL: Salivary Gland, CLONTECH #64026-1;
SKMUS: Skeletal Muscle, CLONTECH #64033-1;
SMINT: Small Intestine, CLONTECH #64039-1;
SPLEN: Spleen, CLONTECH #64034-1;
STOMA: Stomach, CLONTECH #64090-1;
TBAES: Breast (Tumor), CLONTECH #64015-1;
TCERX: Cervix (Tumor), CLONTECH #64010-1;
TCOLN: Colon (Tumor), CLONTECH #64014-1;
TESTI: Testis, CLONTECH #64027-1;
THYMU: Thymus, CLONTECH #64028-1;
TLUNG: Lung (Tumor), CLONTECH #64013-1;
TOVAR: Ovary (Tumor), CLONTECH #64011-1;
TRACH: Trachea, CLONTECH #64091-1;
TUTER: Uterus (Tumor), CLONTECH #64008-1;
UTERU: Uterus, CLONTECH #64029-1;
ADIPS: Adipose, Invitrogen #D6005-01;
BLADE: Bladder, Invitrogen #D6020-01;
BRALZ: Cerebral cortex from an Alzheimer patient (Brain, cortex, Alzheimer), Invitrogen #D6830-01;
CERVX: Cervix, Invitrogen #D6047-01;
COLON: Colon, Invitrogen #D6050-0;
NESOP: Esophagus, Invitrogen #D6060-01;
PERIC: Pericardium, Invitrogen #D6105-01;
RECTM: Rectum, Invitrogen #D6110-01;
TESOP: Esophageal (Tumor), Invitrogen #D6860-01;
TKIDN: Kidney (Tumor), Invitrogen #D6870-01;
TLIVE: Liver (Tumor), Invitrogen #D6880-01;
TSTOM: Stomach (Tumor), Invitrogen #D6920-01;
BEAST: Adult breast, STARATAGENE #735044;
FEHRT: Fetal heart, STARATAGENE #738012;
FEKID: Fetal kidney, STARATAGENE #738014;
FELNG: Fetal lung, STARATAGENE #738020;
NOVAR: Adult ovary, STARATAGENE #735260;

BRASW: subtracted library (BRALZ-BRAWH). A cDNA library was constructed from mRNA prepared from tissues of cerebral cortex obtained from an Alzheimer patient [BRALZ: Cerebral cortex from an Alzheimer patient (Brain, cortex, Alzheimer), Invitrogen #D6830-01]; the cDNAs of this library whose nucleotide sequences were shared by those of mRNAs from whole brain tissue [BRAWH: Whole brain, CLONTECH #64020-1] were subtracted by using a Subtract Kit (Invitrogen #K4320-01).

Further, mRNAs extracted and purified as poly A(+) RNAs from the human tissues shown below were purchased. A cDNA library was prepared from an RNA mixture in which the poly A(+) RNA from each tissue had been combined with poly A(−) RNA. The poly A(−) RNA was prepared by removing poly A(+) RNA from the total RNA of whole brain tissue (CLONTECH #64020-1) by using oligo dT cellulose. The library names and the origins are indicated below in the order of "Library name: Origin".

<Purchase of mRNAs of Human Tissues as Poly A+) RNAs>
BRAMY: Brain (amygdala), CLONTECH #6574-1;
BRCAN: Brain (caudate nucleus), CLONTECH #6575-1;
BRCOC: Brain (corpus callosum), CLONTECH #6577-1;
BRHIP: Brain (hippocampus), CLONTECH #6578-1;
BRSSN: Brain (substantia nigra), CLONTECH #6580-1;
BRSTN: Brain (subthalamic nucleus), CLONTECH #6581-1;
BRTHA: Brain (thalamus), CLONTECH #6582-1.

(2) Preparation of cDNA Library cDNA library was prepared from each RNA by the improved method (WO 01/04286) of oligo capping [M. Maruyama and S. Sugano, Gene, 138: 171-174 (1994)]. A series of procedures, BAP (Bacterial Alkaline Phosphatase) treatment, TAP (Tobacco Acid Pyrophosphatase) treatment, RNA ligation, first strand cDNA synthesis and RNA removal, were carried out using the oligo-cap linker (SEQ ID NO: 3; SEQ ID NO: 5455 from prior application) and oligo dT primer (SEQ ID NO: 4; SEQ ID NO: 5456 from prior application), as described in WO 01/04286. Then, the single-stranded cDNA was converted to a double-stranded cDNA by PCR (polymerase chain reaction) using 5' (SEQ ID NO: 5; SEQ ID NO: 5457 from prior application) and 3' (SEQ ID NO: 6; SEQ ID NO: 5458 from prior application) PCR primers, and then digested with SfiI. Then, a fraction of cDNA fragments, typically 2-kb or longer (3-kb or longer in some cases), was unidirectionally cloned into a DraIII-digested pME18SFL3 vector (FIG. 1) (GenBank AB009864, Expression vector); the cDNA library was thus prepared.

The names of cDNA libraries, which were used in the analysis of full-length cDNA sequences, and their origins are shown in Table 2.

TABLE 2

| Library | Type | Origin, etc. |
|---|---|---|
| 3NB69 | Culture cell | NB69 cells (RCB #RCB0480) |
| ADIPS | Tissue | Adipose (Invitrogen #D6005-01) |
| ADRGL | Tissue | Adrenal gland (CLONTECH #64016-1) |
| ASTRO | Primary culture cell | Normal Human Astrocyte NHA5732 (Takara Shuzo #CC2565) |
| BEAST | Tissue | Adult Breast (STARATAGENE #735044) |
| BGGI1 | Culture cell | GI1 cells (RCB #RCB0763) |
| BLADE | Tissue | Bladder (Invitrogen #D6020-01) |
| BNGH4 | Culture cell | H4 cells (ATCC #HTB-148) |
| BRACE | Tissue | Brain, cerebellum (CLONTECH #64035-1) |
| BRALZ | Tissue | Brain, cortex, Alzheimer (Invitrogen #D6830-01) |
| BRAMY | Tissue | Brain, amygdala (CLONTECH #6574-1) |
| BRAWH | Tissue | Brain, whole (CLONTECH #64020-1) |

TABLE 2-continued

| Library | Type | Origin, etc. |
|---|---|---|
| BRCAN | Tissue | Brain, caudate nucleus (CLONTECH #6575-1) |
| BRCOC | Tissue | Brain, corpus callosum (CLONTECH #6577-1) |
| BRHIP | Tissue | Brain, hippocampus (CLONTECH #6578-1) |
| BRSSN | Tissue | Brain, substantia nigra (CLONTECH #6580-1) |
| BRSTN | Tissue | Brain, subthalamic nucleus (CLONTECH #6581-1) |
| BRTHA | Tissue | Brain, thalamus (CLONTECH #6582-1) |
| CD34C | Primary culture cell | CD34+ cells (AllCells, LLC #CB14435M) |
| COLON | Tissue | Colon (Invitrogen #D6050-0) |
| CTONG | Tissue | Tongue, Cancer |
| D3OST | Primary culture cell | CD34+ cells (ODF induction for 3 days) |
| D6OST | Primary culture cell | CD34+ cells (ODF induction for 6 days) |
| D9OST | Primary culture cell | CD34+ cells (ODF induction for 9 days) |
| DFNES | Primary culture cell | Normal Human Dermal Fibroblasts (Neonatal Skin); NHDF-Neo NHDF2564 (Takara Shuzo #CC2509) |
| FCBBF | Tissue | Brain, Fetal |
| FEBRA | Tissue | Brain, Fetal (CLONTECH #64019-1) |
| FEHRT | Tissue | Heart, Fetal (STARATAGENE #738012) |
| FELNG | Tissue | Lung, Fetal (STARATAGENE #738020) |
| HCASM | Primary culture cell | Human coronary artery smooth muscle cells HCASMC (Toyobo #T305K-05) |
| HCHON | Primary culture cell | Human Chondrocytes HC (Toyobo #T402K-05) |
| HEART | Tissue | Heart (CLONTECH #64025-1) |
| HHDPC | Primary culture cell | Human dermal papilla cells HDPC (Toyobo #THPCK-001) |
| HLUNG | Tissue | Lung (CLONTECH #64023-1) |
| IMR32 | Culture cell | IMR32 cells (ATCC #CCL-127) |
| KIDNE | Tissue | Kidney (CLONTECH #64030-1) |
| LIVER | Tissue | Liver (CLONTECH #64022-1) |
| MAMGL | Tissue | Mammary Gland (CLONTECH #64037-1) |
| MESAN | Primary culture cell | Normal human mesangial cells NHMC56046-2 (Takara Shuzo #CC2559) |
| NESOP | Tissue | Esophagus (Invitrogen #D6060-01) |
| NOVAR | Tissue | Adult Ovary (STARATAGENE #735260) |
| NT2NE | Culture cell | NT2 cells concentrated after differenciation (NT2 Neuron) |
| NT2RI | Culture cell | NT2 cells treated by growth inhibitor for 2 weeks after RA induction for 5 weeks |
| NT2RP | Culture cell | NT2 cells treated by RA for 5 weeks |
| NTONG | Tissue | Tongue |
| OCBBF | Tissue | Brain, Fetal |
| PANCR | Tissue | Pancreas (CLONTECH #64031-1) |
| PEBLM | Primary culture cell | Human peripheral blood mononuclear cells HPBMC5939 (Takara Shuzo #CC2702) |
| PERIC | Tissue | Pericardium (Invitrogen #D6105-01) |
| PLACE | Tissue | Placenta |
| PROST | Tissue | Prostate (CLONTECH #64038-1) |
| PUAEN | Primary culture cell | Human pulmonary artery endothelial cells (Toyobo #T302K-05) |
| RECTM | Tissue | Rectum (Invitrogen #D6110-01) |
| SALGL | Tissue | Salivary Gland (CLONTECH #64026-1) |
| SKMUS | Tissue | Skeletal Muscle (CLONTECH #64033-1) |
| SKNMC | Culture cell | SK-N-MC cells (ATCC #HTB-10) |
| SKNSH | Culture cell | SK-N-SH cells (RCB #RCB0426) |
| SMINT | Tissue | Small Intestine (CLONTECH #64039-1) |
| SPLEN | Tissue | Spleen (CLONTECH #64034-1) |
| STOMA | Tissue | Stomach (CLONTECH #64090-1) |
| SYNOV | Tissue | Synovial membrane tissue from rheumatioid arthritis |
| TBAES | Tissue | Breast, Tumor (CLONTECH #64015-1) |
| TCOLN | Tissue | Colon, Tumor (CLONTECH #64014-1) |
| TESOP | Tissue | Esophageal, Tumor (Invitrogen #D6860-01) |
| TESTI | Tissue | Testis (CLONTECH #64027-1) |
| THYMU | Tissue | Thymus (CLONTECH #64028-1) |
| TKIDN | Tissue | Kidney, Tumor (Invitrogen #D6870-01) |
| TOVAR | Tissue | Ovary, Tumor (CLONTECH #64011-1) |
| TRACH | Tissue | Trachea (CLONTECH #64091-1) |
| TSTOM | Tissue | Stomach, Tumor (Invitrogen #D6920-01) |
| TUTER | Tissue | Uterus, Tumor (CLONTECH #64008-1) |
| UMVEN | Primary culture cell | Human umbilical vein endothelial cells HUVEC (Toyobo #T200K-05) |
| UTERU | Tissue | Uterus (CLONTECH #64029-1) |

The cDNA library with the high fullness ratio (the fullness ratio of 5'-end, which was calculated for each cDNA library by using the protein coding region found in known mRNA species as an index, was 90% in average) prepared by the improved oligo-capping method was constructed by using a eukaryotic expression vector pME18SFL3. The vector contains SR α promoter and SV40 small t intron in the upstream of the cloning site, and SV40 polyA added signal sequence site in the downstream. As the cloning site of pME18SFL3 has asymmetrical DraIII sites, and the ends of cDNA fragments contain SfiI sites complementary to the DraIII sites, the cloned cDNA fragments can be inserted into the downstream of the SR α promoter unidirectionally. Therefore, clones containing full-length cDNA can be expressed transiently by introducing the obtained plasmid directly into COS cells, etc. Thus, the clones can be analyzed very easily in terms of the proteins that are the gene products of the clones, or in terms of the biological activities of the proteins.

(3) Assessment of the 5'-End Completeness of Clones Derived from The cDNA Library Prepared by Oligo-Capping With respect to the plasmid DNAs of clones derived from the libraries, the nucleotide sequences of cDNA 5'-ends (3'-ends as well in some cases) were determined in a DNA sequencer (ABI PRISM 3700, PE Biosystems), after sequencing reaction was conducted by using a DNA sequencing reagent (BigDye Terminator Cycle Sequencing FS Ready Reaction Kit, PE Biosystems) according to the manual. A database was constructed based on the obtained data.

The 5'-end completeness of about 1110,000 clones derived from the human cDNA libraries prepared by the improved oligo-capping method was determined by the following method. The clones whose 5'-end sequences were consistent with those of known human mRNA in the public database were judged to be "full-length" if they had a longer 5'-end sequence than that of the known human mRNA; or even though the 5'-end sequence was shorter, if it contained the translation initiation codon it was judged to have the "full-length" sequence. Clones which did not contain the translation initiation codon were judged to be "not-full-length". The fullness ratio ((the number of full-length clones)/(the number of full-length and not-full-length clones)) at the 5'-end of the cDNA clones was determined by comparing with known human mRNA. As a result, the fullness ratio of the 5'-ends was 90%. The result indicates that the fullness ratio at the 5'-end sequence was extremely high in the human cDNA clones obtained by the oligo-capping method.

EXAMPLE 2

Sequencing Analysis of cDNA Ends and Selection of Full-Length Clones

With respect to the plasmid DNAs of clones obtained from each cDNA library, the 5'-end nucleotide sequences of the cDNAs were determined in a DNA sequencer (ABI PRISM 3700, PE Biosystems), after sequencing reaction was conducted by using a DNA sequencing reagent (Dye Terminator Cycle Sequencing FS Ready Reaction Kit, dRhodamine Terminator Cycle Sequencing FS Ready Reaction Kit or BigDye Terminator Cycle Sequencing FS Ready Reaction Kit, PE Biosystems) according to the manual. A database was constructed using the data obtained.

For the analyzed 5'-end sequences of cDNA clones, the data with the annotation of "complete cds" in the GenBank and UniGene were searched by BLAST homology search. When identical to certain human mRNA sequences, such cDNA clones were excluded. Then, clustering was carried out. When the identity was 90% or higher, and the length of consensus sequence was 50 base pairs or longer, the cDNA clones were assumed to belong to an identical cluster, and thus clustered. cDNA clones longer in the 5' direction were selected from the members belonging to a cluster; if required, the 3'-end sequences of the selected clones were determined by the same analysis method as used to determine the 5'-end sequences. The data of the end sequences obtained were analyzed, and then the clones forming a sequence contig at 5'- and 3'-ends were excluded. Further, as mentioned above, the data was analyzed again by BLAST homology search; when identical to certain human mRNA sequences (including sequences patented and applied for), the cDNA clones were excluded. Thus, the cDNAs clones to be analyzed for their nucleotide sequence were obtained.

EXAMPLE 3

Analysis of the Full-Length Nucleotide Sequences

The full-length nucleotide sequences of the selected clones were determined. The nucleotide sequence determination was mainly performed by primer walking method comprising the dideoxy terminator method using custom-made synthetic DNA primers. Namely, the nucleotide sequences of the DNAs were determined in a sequencer from PE Biosystems, after sequencing reaction was carried out with a DNA sequencing reagent from the same supplier using the custom-made synthetic DNA primers according to the manual. A part of the clones were analyzed with a DNA sequencer from Licor.

Further, the nucleotide sequences of a part of the clones were determined by the shotgun method where the plasmids containing the cDNAs were digested at random were used, instead of the use of custom-made primers, by the same method in the DNA sequencer. The full-length nucleotide sequences were finally determined by completely assembling the partial nucleotide sequences obtained by the above method.

Then, the regions translatable to proteins were deduced from the determined full-length nucleotide sequences, and thereby the amino acid sequences were determined. SEQ ID NOs corresponding to the respective sequences are shown in Table 1.

EXAMPLE 4

Functional Prediction by Homology Search

For the determined nucleotide sequences, GenBank, SwissProt, UniGene, and nr were searched by BLAST. The clones exhibiting higher homology, which were convenient to predict their functions based on the nucleotide sequences and deduced amino acid sequences, were selected based on the BLAST search hit data whose P value or E value was 10-4 or lower and for which the length of consensus sequence×homology=30 or higher in the amino acid database search. Further, from them, representative clones were selected, which are shown as Homology Search Result Data in the last part herein. Accordingly, the data shown herein are merely the representative data, and the molecule exhibiting homology to each clone is not limited thereto. Further, with respect to a part of clones, the BLAST search hit data that did not meet the criteria as described above are not shown herein.

EXAMPLE 5

Search for Signal Sequence, Transmembrane Domain and Other Functional Domains in the Deduced Amino Acid Sequences With respect to the amino acid sequences deduced from the full-length nucleotide sequences, the prediction was made for the presence of signal sequence at the amino terminus, the presence of transmembrane domain, and the presence of functional protein domains (motifs). The signal sequence at the amino terminus was searched for by PSORT [K. Nakai & M. Kanehisa, Genomics, 14: 897-911(1992)]; the transmembrane domain, by SOSUI [T. Hirokawa et al., Bioinformatics, 14: 378-379 (1998)] (Mitsui Knowledge Industry); the function domain, by Pfam (avalible on the world wide web at sanger.ac.uk/Software/Pfam/index.shtml). The amino acid sequence in which the signal sequence at the amino terminus or transmembrane domain had been predicted to be present by PSORT or SOSUI were assumed to be a secretory or membrane protein. Further, when the amino acid sequence hit a certain functional domain by the Pfam functional domain search, the protein function can be predicted based on the hit data, for example, by referring to the function categories on the PROSITE (avalible on the world wide web expasy.ch/cgi-bin/prosite-list.pl). In addition, the functional domain search can also be carried out on the PROSITE.

The search results obtained with the respective programs are as follows for clone HEART20049410:

The deduced amino acid sequence of clone HEART20049410 was detected to have a signal sequence by PSORT.

The deduced amino acid sequence of clone HEART20049410 was determined to have no transmembrane domains by SOSUI.

The deduced amino acid sequence of HEART20049410 was not detected to have a functional domain identified with Pfam.

EXAMPLE 6

Functional Categorization Based on the Full-Length Nucleotide Sequences

The functional prediction and categorization of the proteins encoded by the clones were carried out based on the result of homology search of the databases of GenBank, Swiss-Prot, UniGene and nr (see the Homology Search Result Data) for the full-length nucleotide sequences and the result of domain search of the amino acid sequences deduced from the full-length nucleotide sequences (see Example 5).

The clone predicted to belong to the category of secretory protein/membrane protein means a clone having hit data with some annotation, such as growth factor, cytokine, hormone, signal, transmembrane, membrane, extracellular matrix, receptor, G-protein coupled receptor, ionic channel, voltage-gated channel, calcium channel, cell adhesion, collagen, connective tissue, etc., suggesting that it is a secretory or membrane protein, or means a clone in which the presence of nucleotide sequence encoding a signal sequence or transmembrane domain was suggested by the results of PSORT and SOSUI analyses for deduced ORF.

The clone predicted to belong to the category of glycoprotein-related protein means a clone having hit data with some annotation, such as glycoprotein, suggesting that the clone encodes a glycoprotein-related protein.

The clone predicted to belong to the category of signal transduction-related protein means a clone having hit data with some annotation, such as serine/threonine-protein kinase, tyrosine-protein kinase, SH3 domain, SH2 domain, etc., suggesting that the clone encodes a signal transduction-related protein.

The clone predicted to belong to the category of transcription-related protein means a clone having hit data with some annotation, such as transcription regulation, zinc finger, homeobox, etc., suggesting that the clone encodes a transcription-related protein.

The clone predicted to belong to the category of disease-related protein means a clone having hit data with some annotation, such as disease mutation, syndrome, etc., suggesting that the clone encodes a disease-related protein, or means a clone whose full-length nucleotide sequence has hit data for Swiss-Prot, GenBank, or UniGene, where the hit data corresponds to genes or proteins which have been deposited in the Online Mendelian Inheritance in Man (OMIM) (available on the world wide web at ncbi.nlm.nih.gov/Omim/), which is the human gene and disease database.

The clone predicted to belong to the category of enzyme and/or metabolism-related protein means a clone having hit data with some annotation, such as metabolism, oxidoreductase, E. C. No. (Enzyme commission number), etc., suggesting that the clone encodes an enzyme and/or metabolism-related protein.

The clone predicted to belong to the category of cell division and/or cell proliferation-related protein means a clone having hit data with some annotation, such as cell division, cell cycle, mitosis, chromosomal protein, cell growth, apoptosis, etc., suggesting that the clone encodes a cell division and/or cell proliferation-related protein.

The clone predicted to belong to the category of cytoskeleton-related protein means a clone having hit data with some annotation, such as structural protein, cytoskeleton, actin-binding, microtubles, etc., suggesting that the clone encodes a cytoskeleton-related protein.

The clone which is predicted to belong to the category of nuclear protein and/or RNA synthesis-related protein means a clone having hit data with some annotation, such as nuclear protein, RNA splicing, RNA processing, RNA helicase, polyadenylation, etc., suggesting that the clone encodes a nuclear protein and/or RNA synthesis-related protein.

The clone predicted to belong to the category of protein synthesis and/or transport-related protein means a clone having hit data with some annotation, such as translation regulation, protein biosynthesis, amino-acid biosynthesis, ribosomal protein, protein transport, signal recognition particle, etc., suggesting that the clone encodes a protein synthesis and/or transport-related protein.

The clone predicted to belong to the category of cellular defense-related protein means a clone having hit data with some annotation, such as heat shock, DNA repair, DNA damage, etc., suggesting that the clone encodes a cellular defense-related protein.

The clone predicted to belong to the category of development and/or differentiation-related proteins means a clone having hit data with some annotation, such as developmental protein, etc., suggesting that the clone encodes a development and/or differentiation-related protein.

The clone predicted to belong to the category of DNA-binding and/or RNA-binding protein means a clone having hit data with some annotation, such as DNA-binding, RNA-binding, etc.

The clone predicted to belong to the category of ATP-binding and/or GTP-binding protein means a clone having hit data with some annotation, such as ATP-binding, GTP-binding, etc.

In this functional categorization, when a single clone corresponded to multiple categories of those shown above, the clone was assigned to the multiple categories. However, the function of a protein is not restricted to the functional category in this classification, and there is the possibility that other functions are newly assigned to the protein.

The HEART20049410 clone was predicted to belong to the following categories:
(1) secretory protein and/or membrane protein; and
(2) disease-related protein.

EXAMPLE 7

Expression Frequency Analysis in Silico

The cDNA libraries derived from various tissues and cells as indicated in Example 1 were prepared, and cDNA clones were selected from each library at random. The 5'-end sequences were determined and the database was constructed based on the data. The database was constructed based on the nucleotide sequences of 1,402,070 clones, and thus the population of the database is large enough for the analysis.

Then, clones having a homologous sequence are categorized into a single cluster (clustering) by searching the nucleotide sequences of respective clones in this database with the program of nucleotide sequence homology search; the number of clones belonging to each cluster was determined and normalized for every library; thus, the ratio of a certain gene in each cDNA library was determined. This analysis gave the information of the expression frequency of genes in tissues and cells which were sources of the cDNA libraries.

Then, in order to analyze the expression of a gene containing the nucleotide sequence of the cDNA of the present invention in tissues and cells, the library derived from a tissue or a cell used in the large-scale cDNA analysis was subjected to the comparison of the expression levels between tissues or cells. Namely, the expression frequency was analyzed by comparing the previously normalized values between tissues and/or cells for which the nucleotide sequences of 600 or more cDNA clones had been analyzed. By this analysis, some of the genes were revealed to be involved in the pathology and functions indicated below. Each value in Tables 3 to 51 shown below represents a relative expression frequency; the higher the value, the higher the expression level.

Osteoporosis-Related Genes

Osteoporosis is a pathology in which bones are easily broken owing to overall decrease in components of bone. The onset involves the balance between the functions of osteoblast producing bone and osteoclast absorbing bone, namely bone metabolism. Thus, the genes involved in the increase of osteoclasts differentiating from precursor cells of monocyte/macrophage line (Molecular Medicine 38. 642-648. (2001)) are genes involved in osteoporosis relevant to bone metabolism.

A nucleotide sequence information-based analysis was carried out to identify the genes whose expression frequencies are higher or lower in CD34+ cell (cell expressing a glycoprotein CD34) treated with the osteoclast differentiation factor (Molecular Medicine 38. 642-648. (2001)) than in the untreated CD34+ cell, which is the precursor cell of monocyte/macrophage line. The result of comparative analysis for the frequency between the two cDNA libraries prepared from the RNA of CD34+ cells (CD34C) and from the RNA of CD34+ cells treated with the osteoclast differentiation factor (D30ST, D60ST or D90ST) showed that the HEART20049410 expression levels were not detected as being different between the two conditions.

Genes involved in neural cell differentiation are useful for treating neurological diseases. Genes with varying expression levels in response to induction of cellular differentiation in neural cells are thought to be involved in neurological diseases.

A survey was performed for genes whose expression levels are varied in response to induction of differentiation (stimulation by retinoic acid (RA) or growth inhibitor treatment after RA stimulation) in cultured cells of a neural strain, NT2. The result of comparative analysis of cDNA libraries derived from undifferentiated NT2 cells (NT2RM) and the cells subjected to the differentiation treatment (NT2RP, NT2R1 or NT2NE) showed that the HEART20049410 expression levels were not detected as being different between the two conditions.

Cancer-Related Genes

It has been assumed that, distinct from normal tissues, cancer tissues express a distinct set of genes, and thus the expression can contribute to the carcinogenesis in tissues and cells. Thus, the genes whose expression patterns in cancer tissues are different from those in normal tissues are cancer-related genes. Search was carried out for the genes whose expression levels in cancer tissues were different from those in normal tissues.

The result of comparative analysis of cDNA libraries derived from breast tumor (TBAES) and normal breast (BEAST) showed that the HEART20049410 expression levels were not detected as being different between the two conditions.

The result of comparative analysis of cDNA libraries derived cervical tumor (TCERX) and normal cervical duct (CERVX) showed that the HEART20049410 expression levels were not detected as being different between the two conditions.

The result of comparative analysis of cDNA libraries derived from colon tumor (TCOLN) and normal colon (COLON) showed that the HEART20049410 expression levels were not detected as being different between the two conditions.

The result of comparative analysis of cDNA libraries derived from esophageal tumor (TESOP) and normal esophagus (NESOP) showed that the HEART20049410 expression levels were not detected as being different between the two conditions.

The result of comparative analysis of cDNA libraries derived from kidney tumor (TKIDN) and normal kidney (KIDNE) showed that the HEART20049410 expression levels were not detected as being different between the two conditions.

The result of comparative analysis of cDNA libraries derived from liver tumor (TLIVE) and normal liver (LIVER) showed that the HEART20049410 expression levels were not detected as being different between the two conditions.

The result of comparative analysis of cDNA libraries derived from lung tumor (TLUNG) and normal lung (HLUNG) showed that the HEART20049410 expression levels were not detected as being different between the two conditions.

The result of comparative analysis of cDNA libraries derived from ovary tumor (TOVER) and normal ovary (NOVER) showed the HEART20049410 expression levels were not detected as being different between the two conditions.

The result of comparative analysis of cDNA libraries derived from stomach tumor (TSTOM) and normal stomach (STOMA) showed that the HEART20049410 expression levels were not detected as being different between the two conditions.

The result of comparative analysis of cDNA libraries derived from uterine tumor (TUTER) and normal uterus (UTERU) showed that the HEART20049410 expression levels were not detected as being different between the two conditions.

The result of comparative analysis of cDNA libraries derived from tongue cancer (CTONG) and normal tongue (NTONG) showed that the HEART20049410 expression levels were not detected as being different between the two conditions.

Further, there is a method to search for genes involved in development and differentiation: the expression frequency analysis in which the expression levels of genes are compared between developing or differentiating tissues and/or cells and adult tissues and/or cells. The genes involved in tissue development and/or differentiation are genes participating in tissue construction and expression of function, and thus are useful genes, which are available for regenerative medicine aiming at convenient regeneration of injured tissues.

Search was carried out for the genes whose expression frequencies were different between developing and/or differentiating tissues and/or cells, and adult tissues and/or cells, by using the information of gene expression frequency based on the database of the nucleotide sequences of 1,402,070 clones shown above.

The result of comparative analysis of cDNA libraries derived from fetal brain (FCBBF, FEBRA or OCBBF) and adult brain (BRACE, BRALZ, BRAMY, BRAWH, BRCAN, BRCOC, BRHIP, BRSSN, BRSTN or BRTHA) showed that the HEART20049410 expression levels were not detected as being different between the two conditions.

The result of comparative analysis of cDNA libraries derived from fetal heart (FEHRT) and adult heart (HEART) showed that the genes whose expression levels were different between the two were the following clones (Table 3).

FEHRT20003250, OCBBF20189560, BRAWH20029630, CTONG20150910, HCHON20007510, HEART20003060, HEART20005410, HEART20021840, HEART20025980, HEART20034320, HEART20037810, HEART20049400, HEART20049410, HEART20049800, HEART20061950, HEART20063340, HEART20067870, HEART20067890, HEART20072310, HEART20074430, HEART20077670, HEART20089940, HEART20090000, HEART20095990, HLUNG10000550, HLUNG20017120, KIDNE20028390, KIDNE20028830, NTONG20029480, OCBBF10001750, PROST20127800, SKMUS20001980, SKMUS20003610, SMINT20026890, SMINT20121220, SMINT20122910, SMINT20183530, SPLEN20008740, SPLEN20027440, SPLEN20162680, STOMA20062290, TESTI20254220, THYMU20271250, TRACH20141240, UTERU20004240

The result of comparative analysis of cDNA libraries derived from fetal kidney (FEKID) and adult kidney (KIDNE) showed that the HEART20049410 expression levels were not detected as being different between the two conditions.

The result of comparative analysis of cDNA libraries derived from fetal lung (FELNG) and adult lung (HLUNG) showed that the HEART20049410 expression levels were not detected as being different between the two conditions.

These data show that HEART20049410 is involved in regeneration of tissues and/or cells.

EXAMPLE 8

Expression Frequency Analysis by PCR

Specific PCR primers were prepared based on the full-length nucleotide sequences, and the expression frequency was analyzed by the ATAC-PCR method (Adaptor-tagged competitive PCR method: Nucleic Acids Research 1997, 25(22): 4694-4696; "DNA Micro-array and Advanced PCR Techniques", Cell Technology, supplement, Eds., Muramatsu and Nawa (Shujunsha, 2000): 104-112). Inflammation-related genes can be identified by revealing the genes whose expression levels are altered depending on the presence of an inflammation-inducing factor. Then, by using THP-1 cell line, which is a cell line of monocyte line, and TNF-α, which is inflammation-inducing factor, suitable for this system, the genes whose expression levels are altered depending on the presence of the factors were searched for by the system.

THP-1 cell line (purchased from DAINIPPON PHARMACEUTICAL) was cultured to be confluent in RPMI1640 medium (sigma) containing 5% fetal calf serum (GIBCO BRL). Then, the medium was changed with the medium containing 10 ng/ml TNF-α (human recombinant TNF-α; Pharmacia Biotech), and the culture was continued at 37° C. under 5% $CO_2$. After three hours, the cells were harvested, and total RNA was extracted from them by using ISOGEN reagent (Nippon Gene). The extraction was carried out according to the method in the document attached to ISOGEN reagent. In addition, total RNA was also extracted from the cells cultured without stimulation of TNF-α.

The genes involved in the onset of gastritis and gastroduodenal ulcer induced by the infection of *Helicobacter pylori* to the epithelia of stomach can be identified by revealing the genes whose expression levels are altered depending on co-culturing the cells with *Helicobacter pylori*. A recent study has suggested that various substances derived from *Helicobacter pylori* trigger the inflammation reaction. In particular, the members belonging to the family of genes called "cag pathogenicity island (cag PAI)" contribute to the activation of the NF-κB pathway (Gastroenterology 2000, 119: 97-108). Further, it has been found that cag PAI is involved in the onset of gastritis and the like by the study using an animal model (Journal of Experimental Medicine 2000, 192:1601-1610). Then, by using co-culture of a gastric cancer cell line with cag PAI-positive *Helicobacter pylori* (TN2), suitable for this system, the genes whose expression levels are altered depending on the presence of *Helicobacter pylori* were searched for by the system. Further, in order to study the involvement of cag PAI in the alterations of gene expression levels depending on the co-culture with *Helicobacter pylori*, the altered expression levels were compared between the cells co-cultured with a strain of *Helicobacter pylori* (TN2ΔcagE strain) having a mutation in cagE, which is one of the cag PAI genes, and the cag PAI-positive strain (TN2).

A gastric cancer cell line MKN45 (provided by the Cell Bank, RIKEN GENE BANK, The Institute of Physical and Chemical Research) was cultured to be confluent in RPMI1640 medium (sigma) containing 10% fetal calf serum (GIBCO BRL). Then, the medium was changed with the medium containing 100-fold excess (in terms of the number of cells or the number of colonies) of *Helicobacter pylori* (cag PAI positive strain (TN2) and cagE mutant (TN2ΔcagE): both were provided by Prof. Omata, Faculty of Medicine, The University of Tokyo), as compared with the number of the cancer cells. The culture was continued at 37° C. under 5% $CO_2$. After three hours, the cells were harvested, and total RNA was extracted from them by using ISOGEN reagent (Nippon Gene). The extraction was carried out according to the method in the document attached to ISOGEN reagent. In addition, total RNA was also extracted from the cells cultured without *Helicobacter pylori*.

The analysis by the ATAC-PCR method was carried out basically according to "DNA Micro-array and Advanced PCR Techniques", Cell Technology, supplement (Genome Science Series 1, Eds., Muramatsu and Nawa (Shujunsha, 2000): 104-112). Adapter ligation to the internal standard sample (sample to make the calibration curve for the clone of interest) and test sample was carried out in the two separate reaction systems indicated below. The combination of 6 types of adapters (AD-1, AD-2, AD-3, AD-4, AD-5 and AD-6: see the sequences indicated below) and the samples are as follows.

Reaction System A
AD1; internal standard, 10-fold
AD2; THP-1 cells, unstimulated
AD3; internal standard, 3-fold
AD4; THP-1 cells, TNF-α stimulation for one hour
AD5; THP-1 cells, TNF-α stimulation for three hours
AD6; internal standard, 1-fold Reaction System B
AD1; internal standard, 1-fold
AD2; MKN45 cells, unstimulated
AD3; internal standard, 3-fold
AD4; MKN45 cells, co-cultured with TN2(*Helicobacter pylori*)
AD5; internal standard, 10-fold
AD6; MKN45 cells, co-cultured with TN2ΔcagE (cagE gene mutant)

The internal standard sample used for this assay was a mixture of total RNAs from tissues (or culture cells; all from UNITECH) of Fetal Brain, Testis, Trachea, and Spleen. RNA was prepared according to the standard method.

The sequences of primers specific to the genes and the names of clones of interest in the analysis are as follows. The gene specific primers were designed to produce the PCR products of 70 to 200 bp, which are derived from the adapter-containing cDNA. PCR was basically carried out with a cycling profile of preheating at 94° C. for 3 minutes, and 35 or 40 cycles of denaturation at 94° C. for 30 seconds/annealing at 50° C. for 60 seconds/extension at 72° C. for 90 seconds.

The nucleotide sequences of clone specific primers used in the experiments Clone name, primer sequence and SEQ ID NO are indicated below in this order. Each is demarcated by a double slash mark (//). For a clone for which a primer used in Reaction system A (THP-1 cells) was different from a primer used in Reaction system B (MKN45 cells).

The result of expression frequency analysis show the HEART20049410 expression levels were not detected as being different between the conditions. The clones not shown in the table contain clones whose expression levels could not be measured because the levels were too low or the sizes of the PCR products were different from the expected. It was confirmed that the expression levels of IL-8 genes used as positive control genes were elevated.

The result obtained by the search for the genes whose expression levels were altered depending on the presence of TNF-α in culturing THP-1 cell, which is a human monocyte cell line, showed that the clones whose expression levels were elevated by twofold or more one or three hours after the stimulation (the clones whose expression levels were 0.1 or lower both before and after the stimulation were excluded), did not include the HEART20049410.

On the other hand, in particular cases where the expression levels were relatively high in the unstimulated cells (the relative value was 1 or higher), the clones whose expression levels were decreased by twofold or more by the TNF-α stimulation (the clones whose expression levels were increased 1 or 3 hours after the stimulation were excluded) did not include HEART20049410.

The result obtained by the search for the genes whose expression levels were altered depending on co-culturing gastric cancer cell line MKN45 with cag PAI positive *Helicobacter pylori* (TN2), showed that the HEART20049410 expression levels were not detected as being different between the two conditions.

TABLE 3

| Clone ID | FEHRT | HEART |
|---|---|---|
| FEHRT20003250 | 100 | 0 |
| OCBBF20189560 | 35.243 | 0 |
| BRAWH20029630 | 0 | 79.6 |
| CTONG20150910 | 0 | 5.418 |
| HCHON20007510 | 0 | 23.818 |
| HEART20003060 | 0 | 90.384 |
| HEART20005410 | 0 | 53.555 |
| HEART20021840 | 0 | 100 |
| HEART20025980 | 0 | 100 |
| HEART20034320 | 0 | 100 |
| HEART20037810 | 0 | 100 |
| HEART20049400 | 0 | 100 |
| HEART20049410 | 0 | 63.375 |
| HEART20049800 | 0 | 100 |
| HEART20061950 | 0 | 63.227 |
| HEART20063340 | 0 | 100 |
| HEART20067870 | 0 | 100 |
| HEART20067890 | 0 | 100 |
| HEART20072310 | 0 | 32.316 |
| HEART20074430 | 0 | 100 |
| HEART20077670 | 0 | 100 |
| HEART20089940 | 0 | 100 |
| HEART20090000 | 0 | 68.952 |
| HEART20095990 | 0 | 100 |
| HLUNG10000550 | 0 | 3.611 |
| HLUNG20017120 | 0 | 21.996 |
| KIDNE20028390 | 0 | 48.974 |
| KIDNE20028830 | 0 | 15.131 |
| NTONG20029480 | 0 | 44.44 |
| OCBBF10001750 | 0 | 48.053 |
| PROST20127800 | 0 | 48.531 |
| SKMUS20001980 | 0 | 21.074 |
| SKMUS20003610 | 0 | 7.134 |
| SMINT20026890 | 0 | 7.842 |
| SMINT20121220 | 0 | 23.322 |
| SMINT20122910 | 0 | 30.763 |
| SMINT20183530 | 0 | 65.405 |
| SPLEN20008740 | 0 | 3.252 |
| SPLEN20027440 | 0 | 14.879 |
| SPLEN20162680 | 0 | 2.882 |
| STOMA20062290 | 0 | 40.108 |
| TESTI20254220 | 0 | 16.559 |
| THYMU20271250 | 0 | 3.582 |
| TRACH20141240 | 0 | 6.886 |
| UTERU20004240 | 0 | 5.666 |

Alteration of the expression level of each clone due to TNF-α stimulation to human monocyte cell line THP-1 and alteration of the expression level of each clone due to co-culture of gastric cancer cell line MKN45 with *Helicobacter pylori*. ctl, TNF__1h, and TNF__3h in the column of THP-1, respectively, indicate the relative mRNA expression levels in unstimulated THP-1, in the cell stimulated with 10 ng/mL TNF-α for 1 hour, and in the cell stimulated with 10 ng/mL TNF-α for 3 hours; ctl, Hp, and AcagE in the column of MKN45 indicate the relative mRNA expression levels in MKN45 cultured without *Helicobacter pylori*, in the cells co-cultured with cag PAI-positive *Helicobacter pylori* (TN2) (at a ratio of MKN45:TN2=1:100 cells (colonies)) for 3 hours, and in the cells co-cultured with the cagE mutant (TN2ΔcagE) (at a ratio of MKN45:TN2ΔcagE=1:100 cells (colonies)) for 3 hours, respectively. [ATAC-PCR].

No change in HEART20049410 expression levels was detected in these experiments.

Homology Search Result Data

Data obtained by the homology search for full-length nucleotide sequences and deduced amino acid sequences.

In the result of the search shown below, both units, aa and bp, are used as length units for the sequences to be compared.

Each data includes Clone name, Definition in hit data, P value, Length of sequence to be compared, Homology, and Accession number (No.) of hit data. These items are shown in this order and separated by a double-slash mark, //.

HEART20049410//Homo sapiens cerberus-related protein (CER1) gene, complete cds.//1.10E-12//144aa//29%AF090189

What is claimed is:

1. An isolated polynucleotide comprising a nucleotide sequence encoding a polypeptide comprising the complete amino acid sequence of SEQ ID NO: 2.

2. A vector comprising the polynucleotide of claim 1.

3. A transformant carrying the vector of claim 2.

4. A transformant carrying the vector of claim 2 in an expressible manner.

5. The isolated polynucleotide of claim 1, comprising the complete nucleotide sequence of SEQ ID NO: 1.

6. A vector comprising the polynucleotide of claim 5.

7. A transformant carrying the vector of claim 6.

8. A transformant carrying the vector of claim 6 in an expressible manner.

* * * * *

SEQUENCE LISTING

```
<160> NUMBER OF SEQ ID NOS: 6

<210> SEQ ID NO 1
<211> LENGTH: 1731
<212> TYPE: DNA
<213> ORGANISM: Homo sapiens

<400> SEQUENCE: 1
agtccggaca gacagacagg cagacagacg cacggacaag cagatgctcc ttggccagct      60
atccactctt ctgtgcctgc ttagcggggc cctgcctaca ggctcaggga ggcctgaacc     120
ccacaccgac ggcgccc                                                    17
ggccctgccc ccactggtgc cagcttctgc ccttgggagc tggaaggcct tctttgggcct   240
gcagaaagcc aggcagctgg ggatgggcag gctgcagcgt gggcaagacg aggtggctgc    300
tgtgactctg ccgctgaacc ctcaggaagt gatccagggg atgtgtaagg ctgtgccctt    360
cgttcaggtg ttctcccggc ccggctgctc agccatacgc ctccgaaatc atctgtgctt    420
tggtcattgc tcctctctct acatccctgg ctcggaccc accccactag tcctgtgcaa     480
cagctgtatg cctgctcgca agcgttgggc acccgtggtc ctgtggtgtc tcactggcag    540
ctcagcctcc cgtcgacggg tgaagatatc caccatgctg atcgagggt gtcactgcag    600
cccaaaagca tgaactgagc atcgtggatg ggtgcacgga gacacgcacc ttggagaaat    660
gagggggagat ggaccaagaa agacgtggac ctggatgatg tactctgggt caagagacca   720
gggatgcagg gttaggcaga caggtcccca gagtcctcac cctgctcccc agacagtaga    780
cacagtgccc gtcctggagt tgcaccactg atagtcacag cacacaatga ttgacaactc    840
cttatattcc gtcatcgctc                                                20
cgcaatctca gctcactgca agctccacct cccgggttta tgccattctc ctgtctcagc    960
ctcccgagta gctgggacta caggcacccg ccaacacgcc cggctaattt ttcgtatttt   1020
tagtaaagac agggtttcac cgtgttagcc aggatggtct ctatctcctg acctcgtgat   1080
ctgcctgcct tggccttatt attttttttt tttaaggaca gagtctctct ctgtcaccca   1140
ggctggagtg caatggcgcg atcttggctc actgtaactt ccacttgcca ggctcaagca   1200
gttctcctgc ctcagcctcc tgagtagctg ggactacagg caccgccac catgcccagc    1260
taattttttgt attttttagta gagacagagt ttcaccatat tagcctggct ggtctcaaac  1320
tcctggcctc aggtgatctg cccacctcgg cctcccaaag tgctgggatc aaatccactg   1380
ttaatcatta ggctgaactg tctcttatag aatgaggtca aagacactcc cagttgcagg    1440
gagggtagat ggccccaccc agaccgagag acacagtgat gacctcagcc tagggacacc   1500
aaaaaaaaaa aaaaaaaaaa cccaaaccaa aaacgcaaac caaagcaggc aggcagacag   1560
tccgtcatcg ctcctcaggg                                                20
ctcttgcctt gatagtggtg ctgtgtccct ctcagacccc ccacctgagt ctccacagag  1680
ccccacgcct ggcatggcat tccacagaaa ccataaaggt tggctgagtc c            1731

<210> SEQ ID NO 2
<211> LENGTH: 189
<212> TYPE: PRT
<213> ORGANISM: Homo sapiens

<400> SEQUENCE: 2
aaaacgtcag ccatggtccc                                                20
                1               5                  10              15
            Leu Pro Thr Gly Ser Gly Arg Pro Glu Pro Gln Ser Pro Arg Pro Gln
                        20                  25

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide
<400> SEQUENCE: 11
ttctcgctgg tgagtttc                                                   18
ttctcctcct ccctggcag                                                  20

<210> SEQ ID NO 12
<211> LENGTH: 20
```

```
<212> TYPE: DNA
<213> ORGANISM: Artificial Sequence
<220> FEATURE:
<223> OTHER INFORMATION: Synthetic oligonucleotide
<400> SEQUENCE: 12
tctcgctggt gagtttc                                                      17
ctggcttctc ctcctcccct                                                   20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide
<400> SEQUENCE: 13
tcccgcctgt gacatgcatt                                                   20
cctgctggct tctcctcctc                                                   20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide
<400> SEQUENCE: 14
tcctcctccc cgcggcgggt                                                   20
tctggcgctg caccactctc                                                   20

<210> SEQ ID NO 15
<211> LENGTH: 20
<212> TYPE: RNA
<213> ORGANISM: Artificial Sequence
<220> FEATURE:
<223> OTHER INFORMATION: Synthetic oligonucleotide
<400> SEQUENCE: 15
ctcgcccgct cctcctcccc                                                   20
uaggagaugc cuaaggcuuu                                                   20

<210> SEQ ID NO 16
<211> LENGTH: 20
<212> TYPE: RNA
<213> ORGANISM: Artificial Sequence
<220> FEATURE:
<223> OTHER INFORMATION: Synthetic oligonucleotide
<400> SEQUENCE: 16
ttctcgcccg ctcctcctcc                                                   20
gcuaugucga cacccaauuc                                                   20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
ttctcctcct ccctggcag                                                    20
<223> OTHER INFORMATION: bases at these positions are RNA

<400> SEQUENCE: 17
cauaggagau gccuaaggct                                                   20

<210> SEQ ID NO 18
<211> LENGTH: 21
<212> TYPE: DNA
<213> ORGANISM: Artificial Sequence
ctggcttctc ctcctcccct                                                   20
```

```
<223> OTHER INFORMATION: Synthetic oligonucleotide
<220> FEATURE:
<221> NAME/KEY: misc_feature
<222> LOCATION: 1-5, 17-21
<223> OTHER INFORMATION: Bases at these positions are RNA

<400> SEQUENCE: 18
gcguutgctc ttcttcuugc g                                      21 cctgctggct tctcctcctc                                        20
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1-6, 15-20
<223> OTHER INFORMATION: Bases at these positions are RNA
<400> SEQUENCE: 19
tctggcgctg caccactctc                                        20
gcguuugctc ttctucuugc g                                      21

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY
```